US007592161B2

(12) United States Patent
Lambowitz et al.

(10) Patent No.: US 7,592,161 B2
(45) Date of Patent: Sep. 22, 2009

(54) METHODS FOR ANALYZING THE INSERTION CAPABILITIES OF MODIFIED GROUP II INTRONS

(75) Inventors: Alan M. Lambowitz, Austin, TX (US); Huatao Guo, Alhambra, CA (US); Michael Karberg, Austin, TX (US)

(73) Assignees: The Ohio State University Research Foundation, Columbus, OH (US); The University of Texas Board of Regents of the University of Texas System, Austin, TX (US)

( * ) Notice: Subject to any disclaimer, the term of this patent is extended or adjusted under 35 U.S.C. 154(b) by 399 days.

(21) Appl. No.: 10/277,643

(22) Filed: Oct. 22, 2002

(65) Prior Publication Data

US 2003/0104352 A1 Jun. 5, 2003

Related U.S. Application Data

(63) Continuation of application No. 09/687,944, filed on Oct. 13, 2000, now abandoned.

(60) Provisional application No. 60/159,724, filed on Oct. 15, 1999.

(51) Int. Cl.
*C12P 19/34* (2006.01)
*C12P 12/06* (2006.01)
(52) U.S. Cl. .............. 435/91.1; 435/69.1; 435/194; 536/23.2; 536/23.4; 536/24.1
(58) Field of Classification Search ................ 435/91.1
See application file for complete search history.

(56) References Cited

U.S. PATENT DOCUMENTS

| | | | |
|---|---|---|---|
| 5,180,818 A | 1/1993 | Cech et al. | |
| 5,498,531 A | 3/1996 | Jarrell | |
| 5,698,421 A | 12/1997 | Lambowitz et al. | |
| 5,804,418 A | 9/1998 | Lambowitz et al. | |
| 5,830,430 A | 11/1998 | Unger et al. | |
| 5,869,634 A | 2/1999 | Lambowitz et al. | |
| 6,001,608 A | 12/1999 | Lambowitz et al. | |
| 6,027,895 A | 2/2000 | Lambowitz et al. | |
| 6,150,160 A * | 11/2000 | Kazazian et al. | ......... 435/320.1 |
| 6,306,596 B1 | 10/2001 | Lambowitz et al. | |
| 2002/0086323 A1 | 7/2002 | Lambowitz et al. | |

FOREIGN PATENT DOCUMENTS

| | | |
|---|---|---|
| AU | 715563 | 5/2000 |
| AU | 739106 | 1/2002 |
| AU | 748237 | 10/2002 |
| EP | 851940 | 7/1998 |
| WO | 9710362 | 3/1997 |
| WO | 9823756 | 6/1998 |
| WO | 9838337 | 9/1998 |
| WO | 9854353 | 12/1998 |
| WO | 9943854 | 9/1999 |
| WO | 0129059 | 4/2001 |
| WO | 2005123937 | 12/2005 |
| WO | 2005123962 | 12/2005 |

OTHER PUBLICATIONS

Mohr et al. Rules for DNA target-site recognition by lactococcal group II intron enable targeting of the intron to specific DNA sequences. Genes and Development 2000, vol. 14: 559-573. Cold Spring Harbor Laboratory Press.*
Jacquier A. Group II introns: Elaborate ribozymes. Biochem 1996, vol. 78: 474-487. Elsevier.*
Rambo et al. Assembly of an Active Group II intron-Maturase complex by Protein Dimerization. Biochemistry 2004, 43: 6486-6497.*
Patil et al. DNA-based Therapeutics and DNA Delivery Systems: A Comprehensive Review. The AAPS Journal 2005, vol. 7(1): E61-E77.*
Wank et al. A reverse transcriptase/maturase promotes splicing by binding at its own coding segment in a group II intron RNA. Molecular Cell, vol. 4, 239-250, Aug. 1999.*
Jones III et al. Retargeting mobile group II introns to repair mutant genes. Molecular Therapy 2005, vol. 11, No. 5, pp. 687-694.*
"Multiple Exon-Binding Sites in Class II Self-Splicing Introns" by Jacquier, et al., *Cell*, vol. 50, 17-29, Jul. 3, 1987.
"Antagonistic Substrate Binding by a Group II Intron Ribozyme" by Qin, et al., *J. Mol. Biol.* (1999) 291, 15-27.
"Sequence Specificity of a Group II Intron Ribozyme: Multiple Mechanisms for Promoting Unusually High Discrimination Against Mismatched Targets" by Xiang, et al., *Biochemistry*, 1998, 37, 3839-3849.
"Self-splicing of the mobile group II intron of the filamentous fungus *Podospora anserina* (COI II) in vitro" by Schmidt, et al., *The EMBO Journal*, vol. 9, No. 7, pp. 2289-2298, 1990.
"Rules for DNA target-site recognition by a lactococcal group II intron enable retargeting of the intron to specific DNA sequences" by Mohr, et al., *Genes & Development*, 14:559-573, 2000.
"A bacterial group II intron encoding reverse transcripase, maturase, and DNA endonuclease activities: biochemical demonstration of maturase activity and insertion of new genetic information within the intron" by Matsuura, et al., *Genes & Development*, 11:2910-2924, 1997.

(Continued)

*Primary Examiner*—Kimberly Chong
(74) *Attorney, Agent, or Firm*—Calfee, Halter & Griswold LLP

(57) ABSTRACT

The present invention provides a system and methods for analyzing the function of nucleotide integrases and modified group II introns. The system comprises a donor plasmid comprising a wild-type or modified group II intron, a recipient plasmid comprising a DNA recognition site and a promoterless reporter gene downstream of the DNA target site, and a host cell. The method comprises the steps of transforming a host cell with the donor and recipient plasmids, assaying for expression of the reporter gene, isolating plasmid DNA from the cotransformed cells, and analyzing the plasmid DNA to confirm that the group II intron has been inserted into the target sequence. The present invention also provides a method for simultaneously analyzing the activity of two or more modified nucleotide integrases. The present invention also relates to methods of preparing a library of donor plasmids containing a plurality of diverse modified group II intron DNA sequences.

18 Claims, 23 Drawing Sheets

OTHER PUBLICATIONS

"Group II Introns Designed to Insert into Therapeutically Relevant DNA Target Sites in Human Cells" by Guo, et al., *Science*, Jul. 21, 2000, vol. 289, pp. 452-457.
Supplementary European Search Report dated Dec. 28, 2005.
"Group II intron endonucleases use both RNA and protein subunits for recognition of specific sequences in double-stranded DNA" by Guo, et al., The EMBO Journal, vol. 16, No. 22, pp. 6835-6848, 1997.
"Efficient Integration of an Intron RNA into double-stranded DNA by reverse splicing" by Yang, et al., Nature, vol. 381, May 23, 1996, pp. 332-335.
"Mobile Group II Introns of Yeast Mitochondrial DNA Are Novel Site-Specific Retroelements" by Moran, et al., Molecular and Cellular Biology, May 1995, vol. 15, No. 5, pp. 2828-2838.
"Regulation of intron function: efficient splicing in vivo of a bacterial group II intron requires a functional promoter within the intron" by Zhou, et al., Molecular Microbiology (2000) 37(3), 639-651.
"A Reverse Transcriptase/Maturase Promotes Splicing by Binding at Its Own Coding Segment in a Group II Intron RNA" by Wank, et al., Molecular Cell, vol. 4, 239-250, Aug. 1999.
Saldanha, R.J., Patel, S.S., Surendran, R., Lee, J.C., and Lambowitz, A.M. Involvement of Neurospora mitochondrial tyrosyl-tRNA synthetase in RNA splicing. A new method for purifying the protein and characterization of physical and enzymatic properties pertinent to splicing. Biochemistry, 34, 1275-1287, 1995.
Lambowitz, A.M., and Chiang, C.-C. The Mauriceville and Varkud plasmids: primitive retroelements found in Neurospora mitochondria. Proceedings Fifth International Congress of Mycology, Vancouver, B.C., Canada, Aug. 1994, Can. J. Botany, 73 (Suppl. 1), S173-S179, 1995.
Kennell, J.C., Saville, B., Mohr, S., Kuiper, M., Sabourin, J.R., Collins, R.A., and Lambowitz, A.M. The VS catalytic RNA replicates by reverse transcription as a satellite of a retroplasmid. Genes & Dev. 9, 294-303, 1995.
Caprara, M.G., Mohr, G., and Lambowitz, A.M. A tyrosyl-tRNA synthetase protein induces tertiary folding of the group I intron catalytic core. J. Mol. Bol. 257, 512-531, 1996.
Saldanha, R., Ellington, A., and Lambowitz, A.M. Analysis of the CYT-18 protein binding site at the junction of stacked helices in a group I intron RNA by quantitative binding assays and in vitro selection. J. Mol. Biol. 261, 23-42, 1996.
Myers, C.A., Wallweber, G.J., Rennard, R., Kemel, Y., Caprara, M.G., Mohr, G., and Lambowitz, A.M. A tyrosyl-tRNA synthetase suppresses structural defects in the two major helical domains of the group I intron catalytic core. J. Mol. Biol. 262, 87-104, 1996.
Caprara, M.G., Lehnert, V., Lambowitz, A.M., and Westhof, E. A tyrosyl-tRNA synthetase recognizes a conserved tRNA-like structural motif in the group I intron catalytic core. Cell, 87, 1135-1145, 1996.
Wallweber, G.J., Mohr, S., Rennard, R., Caprara, M.G., and Lambowitz, A.M. Characterization of Neurospora mitochondrial group I introns reveals different CYT-18 dependent and independent splicing strategies and an alternative 3' splice site for an intron ORF. RNA, 3, 114-131, 1997.
Chiang, C.-C., and Lambowitz, A.M. The Mauriceville retroplasmid reverse transcriptase initiates cDNA synthesis de novo at the 3' end of tRNAs. Mol. Cell. Biol. 17, 4526-4535, 1997.
Chen, B., and Lambowitz, A.M. De novo and DNA primer-mediated initiation of cDNA synthesis by the Mauriceville retroplasmid reverse transcriptase involve recognition of a 3' CCA sequence. J. Mol. Biol. 271, 311-332, 1997.
Yang, J., Mohr, G., Perlman, P.S., and Lambowitz, A.M. Group II intron mobility in yeast mitochondria: target DNA-primed reverse transcription activity of al1 and reverse splicing into DNA transposition sites in vitro. J. Mol. Biol. 282: 505-523, 1998.
Cousineau, B., Smith, D., Lawrence-Cavanagh, S., Mueller, J.E., Yang, J., Mills, D., Manias, D., Dunny, G., Lambowitz, A.M., and Belfort, M., Retrohoming of a bacterial group II intron: mobility via complete reverse splicing independent of homologous recombination. Cell, 54, 451-462, 1998.
Lambowitz, A.M., Caprara, M.G., Zimmerly, S., and Perlman, P.S. Group I and group II ribozymes as RNPs: clues to the past and guides to the future. In: The RNA World, Second Edition (R.F. Gesteland, T.R. Cech, and J.F. Atkins, Editors), pp. 451-485, Cold Spring Harbor Laboratory Press, Cold Spring Harbor, New York, 1999.
Zimmerly, S., Moran, J.V., Perlman, P.S., and Lambowitz, A.M. Group II intron reverse transcriptase in yeast mitochondria. Stabilization and regulation of reverse transcriptase activity by the intron RNA. J. Mol. Biol. 289, 473-490, 1999.
Mohr, G., Smith, D., Belfort, M., and Lambowitz, A.M. Rules for DNA target-site recognition by a lactococcal group II intron enable retargeting of the intron to specific DNA sequences. Genes & Devel. 14, 559-573, 2000.
Mohr, S., Wanner, L.A., Bertrand, H., and Lambowitz, A.M. Characterization of an unusual tRNA-like sequence found inserted in a Neurospora retroplasmid. Nucl. Acids Res. 28, 1514-1524, 2000.
Chen, X., Gutell, R.R., and Lambowitz, A.M. Function of tyrosyl-tRNA synthetase in splicing group I introns. An induced fit model for binding to the P4-P6 domain based on analysis of mutations at the junction of the P4-P6 stacked helices. J. Mol. Biol. 301, 265-283, 2000.
Eskes, R., Liu, L., Ma, H., Chao, M.Y., Dickson, L., Lambowitz, A.M. and Perlman, P.S. Multiple homing pathways used by yeast mitochondrial groups II introns. Mol. Cell. Biol. 20, 8432-8446, 2000.
Bojanowski, K., et al., "Ionic control of chromosome architecture in living and permeabilized cells", Exp. Cell. Res. 244, pp. 286-294, 1998.
Bonitz, et al., "Assembly of the mitochondrial membrane system. Structure and nucleotide sequence of the gene coding for subunit 1 of yeast cytochrome oxidase", J Biological Chemisty, Dec. 25, 1980, vol. 255, No. 24, pp. 11927-11941.
Chen, ZJ et al., "Epigenetic silencing of RNA polymerase I transcription: a role for DNA methylation and histone modification in nucleolar dominance", Gene Dev. 11, pp. 2124-2136, 1997.
Database EMBL, Coxi gene, retrieved from EBI database accession No. V000694 XP002233948 & Database Swall (Online) COXI/OXI3 intron 1 protein, Jul. 21, 1986, retrieved from EBI Database accession No. P03875 XP002233949.
Eskes, et al., "Mobility of Yeast Mitochondiral Group II Introns: Engineering a New Site Specificity and Retrohoming via full reverse splicing", Cell, (in press), May 1997.
Frazier, CL, et al., "Genetic manipulation of Lactococcus lactis by using targeted group II introns: generation of stable insertions without selection", Appl. Environ, Microbiol., 69, pp. 1121-1128, 2003.
Gencheva, M. et al., "Mapping the sites of initiation of DNA replication in rat and human rRNA genes", J. Biol. Chem, 271, pp. 2608-2614, 1996.
Guo et al., "Group II introns as site-specific retroelements", Keystone Symposia on Molecular and Cellular Biology: Transposition and Site-Specific Recombination, Santa Fe, New Mexico, Mar. 1-7, 1997.
Guo, et al., "Targeted DNA cleavage and insertion by group II introns", RNA '97, The second annual meeting of the RNA society, May 27-Jun. 1, 1997, p. 262.
Haas, J. et al, "Codon usage limitation in the expression of HIV-1 envelope glycoprotein", Current Biol. 6, pp. 315-324, 1996.
Haber, JE, "Partners and pathways repairing a double-strand break", Trend in Genetics, 16, pp. 259-264, 2000.
Karberg, M. et al., "Group II introns as controllable gene targeting vectors for genetic manipulation of bacteria", Nat. Biotechnol. 19, pp. 1162-1167, 2001.
Kennell, et al., "Reverse Transcriptage Activity Associated with Maturase-Encoding Group II Introns in Yeast Mitochondria", Cell, vol. 73, pp. 133-146, Apr. 9, 1993.
Lambowitz "Preparation and analysis of mitochondrial ribosomes", Meth. Enzymol. 59, 421-422, 1979.
Lambowitz, et al., "Introns as Mobile Genetic Elements", Annual Reviews Biochem, vol. 62, pp. 587-622, 1993.
Lambowitz et al., "Mitochondrial plasmid and group II intron reverse transcription", Keystone Symposia on Molecular and Cellular Biology: Viral Genome Replication, Tamorron, Colorado, Mar. 1-7, 1996.
Lambowitz, et al., "Novel mechanism for site-specific DNA cleavage and insertion involving group II intron catalytic RNAs", Functional Genomics Conference, Newport, Rhode Island, Nov. 2-5, 1997.

Lazowska et al., "Homing of a group II intron in yeast mitochondrial DNA is accompanied by unidirectional co-conversion of upstream-located markers", The EMBO Journal, England, vol. 13, No. 20, pp. 4963-4972, Oct. 17, 1994.

Mackett et al., General Method for Production and Selection of Infectious Vaccinia Virus Recombinants Expressing Foreign Genes, J vol. 49: 857-864, 1994.

Matsuura, et al., "A bacterial group II intron encoding reverse transcriptase, maturase, and DNA endonuclease activities", RNA '97, The Second annual meeting of the RNA society, May 27-Jun. 1, 1997, p. 369.

Mills, et al., "Splicing of Group II introon involved in the conjugative tansfer of pRS01 in Lactococci", J. of Bacteriology, vol. 178, pp. 3531-3538, Jun. 1996.

Mills, et al., "Homing of a Group II intron from Lactococcus lactis supsp. lactis ML3", Bacteriology, vol. 179, No. 19, pp. 6107-6111, Oct. 1997.

Monoz-Adelantado et al., "Mobility of the Sinorhizobium meliloti Group II Intron RmInt1 Occurs by reverse splicing into DNA, but requires an unknown reverse transcriptase priming mechanism", J Mol Biol 327, 931-943, 2003.

Mohr, et al., "Evolutionary relationships amoung Group II intron-encoded proteins and identification of a conserved domain that may be related to maturase function", Nucleic Acids Research, vol. 21, No. 22, pp. 4991-4997, 1993.

Moran, et al., "Splicing defective mutants of the COXI gene of yeast mitochondrial DNA: Initial definition of the maturase domain of the group intron A12", Nucleic Acids Research, vol. 22, No. 11, 1994, pp. 2057-2064.

Morl, et al., "Integration of Group II Intron b11 into a foreign RNA by Reversal of the self-splicing reaction in vitro", Cell, vol. 60, pp. 629-636, Feb. 23, 1990.

Morris, MC et al., "A peptide carrier for the delivery of biologically active proteins into mammalian cells", Nat. Biotechnol. 19, pp. 1173-1176, 2001.

Neumann, G. et al., "Generation of influenza A viruses entirely from cloned cDNAs", Proc. Natl. Acad. Sci, USA, 96, pp. 9345-9350, 1999.

Palmer, TD et al., "Efficient expression of a protein coding gene under the control of an RNA polymerase I promoter", Nucl. Acids. Res. 21, pp. 3451-3457, 1993.

Rossi et al., "RNA enzymes (ribozymes) as antiviral therapeutic agents", Tibtech, vol. 8, pp. 179-183, Jul. 1990.

Saldanha, et al., "Group I and group II introns", The FASEB Journal, vol. 7, pp. 15-24, Jan. 1993.

Saldanha, Roland et al., "RNA and Protein Catalysis in Group II Intron Splicing and Mobility Reactions Using Purified Components", Biochemistry, 38, pp. 9069-9083, 1999.

Shearman, et al., "Splicing of a group II intron in a functional transfer gene of Lactococcus lactis", Molecular Microbiology, vol. 21, pp. 45-53, Jul. 1996.

Smith, Gr, "Homologous recombination near and far from DNA breaks: alternative roles", Annu. Rev. Genet. 35, pp. 243-274, 2001.

Vagner, S. et al., "Irresistible IRES", EMBO Reports. vol. 21, No. 101, pp. 893-898, 2001.

Yoon, Y. et al., "Mapping of replication initiation sites in human ribosomal DNA by nascent-strand abundance analysis", Mol. Cell. Biol. 15, pp. 2482-2489, 1995.

Zimmerly, et al., "Group II Intron Mobility Occurs to Target DNA-Primed Reverse Transcription", Cell, vol. 82, pp. 545-554, Aug. 25, 1995.

Zimmerly, et al., "A Group II Intron RNA is a Catalytic Component of a DNA Endonuclease Involved in Intron Mobility", Cell, vol. 83, pp. 1-10, Nov. 17, 1995.

Zimmerly, et al., "Retrotransposition of group II introns", Keystone Sumposia on Molecular and Cellular Biology: Viral Genome Replication, Tamarron, Colorado, Mar. 1-7, 1996.

Zimmerly, et al., "Group II intron mobility and evolution", Keystone Symposia on Molecular and Cellular Biology: Postranscriptional RNA Processing, Hilton Head, South Carolina, Mar. 11-17, 1996.

Belfort, "An Expanding Universe of Introns", Science, vol. 262, pp. 1009-1010, Nov. 12, 1993.

Executed Supplemental Information Disclosure Statement of Alan Lambowitz, Apr. 9, 1996.

Executed Supplemental Information Disclosure Statement of Steven Zimmerly, Feb. 22, 1996.

Hutvagner, G. et al., "A cellular function for the RNA-interference enzyme Dicer in the maturation of the let-7 small temproal RNA", Science, 293, pp. 834-838, 2001.

Michel, et al., "Structure and Activites of Group II Introns", Annu Rev Biochem 1995, 64, pp. 435-461.

* cited by examiner

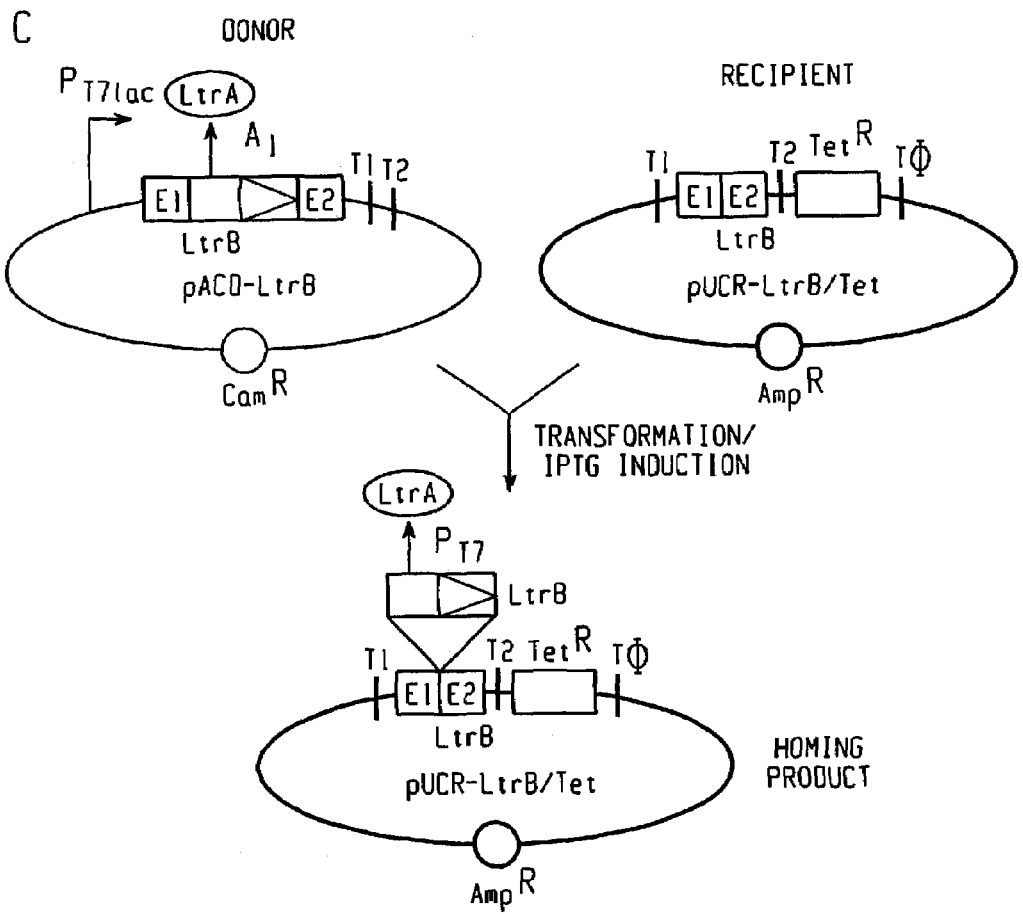
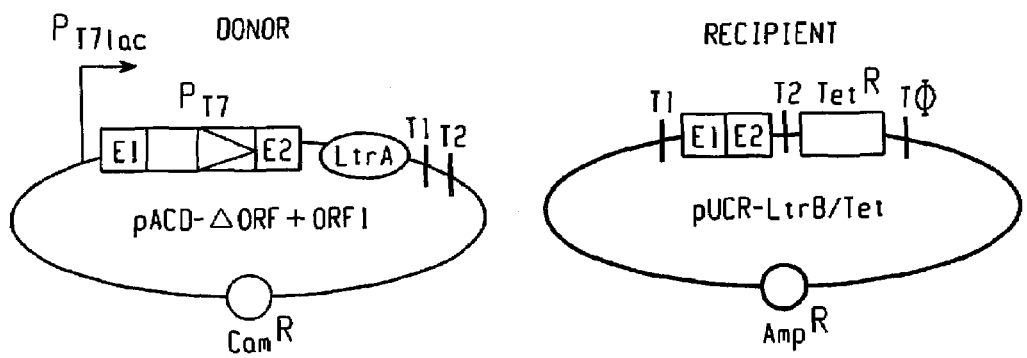
Fig. 1B

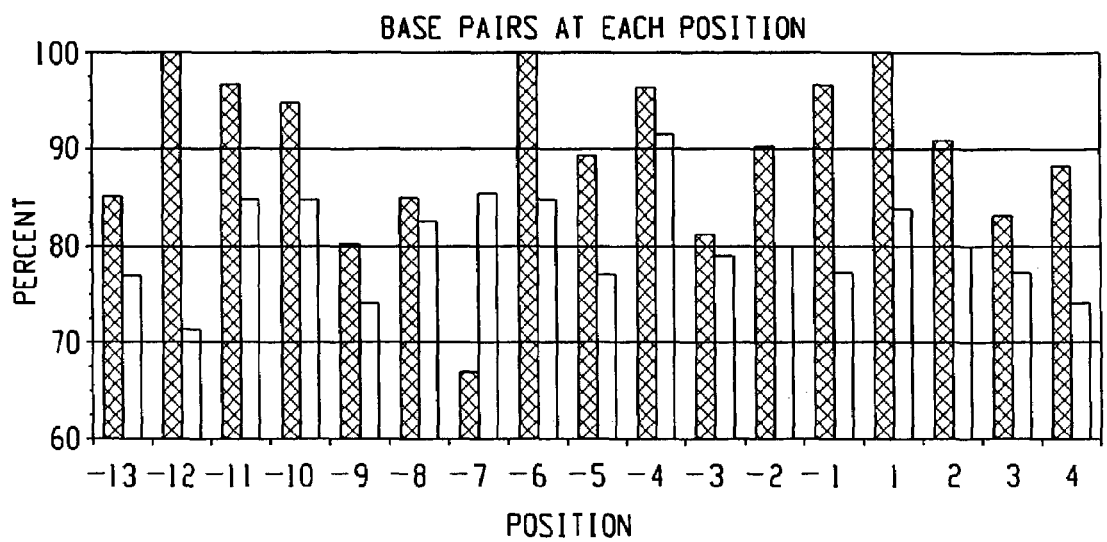
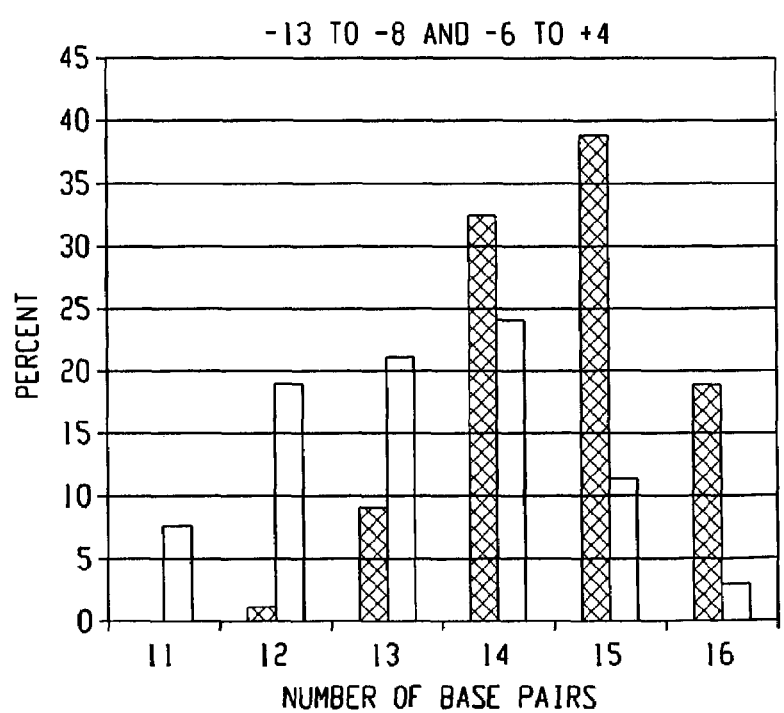
Fig. 3

Fig. 4B

MATCH TO FIG.4C

```
                                          MATCH TO FIG.4E
pBRR-CCR5(s)/Tet              T C A A C T C [T] G A C A [G][G]

CCR5-24s                                                      -20
pBRR-CCR5(s)/Tet              C T [C] G A [C] A [T] G [G] A [T] A [T] C

CCR5-43Ss                                                     -20
pBRR-CCR5(s)/Tet              G [C] T T T A A A A [G] C C A [G][G] A

HIV1-54a/9186a                                                -20
pBRR-HIV1(1-2561a)Tet         [G] C A A G [C] T T T A T [T] G A [G][G]

HIV1-54a/9186a
(corrected)                                                   -20
pBRR-HIV1(1-2561a)/Tet        [G] C A A G [C] T T T A T [T] G A [G][G]

HIV1-2654a                                                    -20
pBRR-HIV1(2562-5371a)/Tet     [C] C A T G T A [T] T [G][A] T A [G] A T

HIV1-2654a
(corrected)                                                   -20
pBRR-HIV1(2562-5371a)/Tet     [C] C A T G T A [T] T [G][A] T A [G] A T
```

Fig. 4F

```
         10        20        30        40        50        60
AAGCTTAGAGAAAAATAATGCGGTGCTTGGTCATCACCTCATCCAATCATTTTCTCCTGA
TTCGAATCTCTTTTTATTACGCCACGAACCAGTAGTGGAGTAGGTTAGTAAAAGAGGACT 70        80        90       100       110       120
TGACAATCTAACTCCTGAACAAATTCATGAAATAGGTCGTCAAACCATATTAGAATTTAC  LtrB, E1
ACTGTTAGATTGAGGACTTGTTTAAGTACTTTATCCAGCAGTTTGGTATAATCTTAAATG 130       140       150       160       170       180
AGGTGGCGAATATGAATTTGTGATTGCAACCCACGTCGATCGTGAACACATCCATAACGT  LtrBI
TCCACCGCTTATACTTAAACACTAACGTTGGGTGCAGCTAGCACTTGTGTAGGTATTGCA 190       200       210       220       230       240
GCGCCCAGATAGGGTGTTAAGTCAAGTAGTTTAAGGTACTACTCTGTAAGATAACACAGA
CGCGGGTCTATCCCACAATTCAGTTCATCAAATTCCATGATGAGACATTCTATTGTGTCT 250       260       270       280       290       300
AAACAGCCAACCTAACCGAAAAGCGAAAGCTGATACGGGAACAGAGCACGGTTGGAAAGC
TTTGTCGGTTGGATTGGCTTTTCGCTTTCGACTATGCCCTTGTCTCGTGCCAACCTTTCG 310       320       330       340       350       360
GATGAGTTACCTAAAGACAATCGGGTACGACTGAGTCGCAATGTTAATCAGATATAAGGT
CTACTCAATGGATTTCTGTTAGCCCATGCTGACTCAGCGTTACAATTAGTCTATATTCCA 370       380       390       400 EBS2 410       420
ATAAGTTGTGTTTACTGAACGCAAGTTTCTAATTTCGGTTATGTGTCGATAGAGGAAAGT
TATTCAACACAAATGACTTGCGTTCAAAGATTAAAGCCAATACACAGCTATCTCCTTTCA
                                          ┌─EBS1
        430       440       450       460 \      470       480
GTCTGAAACCTCTAGTACAAAGAAAGGTAAGTTATGGTTGTGGACTTATCTGTTATCACC
CAGACTTTGGAGATCATGTTTCTTTCCATTCAATACCAACACCTGAATAGACAATAGTGG 490       500       510       520       530       540
ACATTTGTACAATCTGTAGGAGAACCTATGGGAACGAAACGAAAGCGATGCCGAGAATCT
TGTAAACATGTTAGACATCCTCTTGGATACCCTTGCTTTGCTTTCGCTACGGCTCTTAGA 550       560       570       580       590       600
GAATTTACCAAGACTTAACACTAACTGGGGATACCCTAAACAAGAATGCCTAATAGAAAG
CTTAAATGGTTCTGAATTGTGATTGACCCCTATGGGATTTGTTCTTACGGATTATCTTTC
```
MATCH TO FIG. 7B

Fig. 7A

MATCH TO FIG. 7A

```
          610        620        630        640        650        660
GAGGAAAAAGGCTATAGCACTAGAGCTTGAAAATCTTGCAAGGGTACGGAGTACTCGTAG
CTCCTTTTTCCGATATCGTGATCTCGAACTTTTAGAACGTTCCCATGCCTCATGAGCATC 670        680        690        700        710        720
TAGTCTGAGAAGGGTAACGCCCTTTACATGGCAAAGGGGTACAGTTATTGTGTACTAAAA
ATCAGACTCTTCCCATTGCGGGAAATGTACCGTTTCCCCATGTCAATAACACATGATTTT
                                        ┌──→LtrA ORF
          730        740        750    │   760        770        780
TTAAAAATTGATTAGGGAGGAAAACCTCAAAATGAAACCAACAATGGCAATTTTAGAAAG
AATTTTTAACTAATCCCTCCTTTTGGAGTTTTACTTTGGTTGTTACCGTTAAAATCTTTC 790        800        810        820        830        840
AATCAGTAAAAATTCACAAGAAAATATAGACGAAGTTTTTACAAGACTTTATCGTTATCT
TTAGTCATTTTTAAGTGTTCTTTTATATCTGCTTCAAAAATGTTCTGAAATAGCAATAGA 850        860        870        880        890        900
TTTACGTCCAGATATTTATTACGTGGCGTATCAAAATTTATATTCCAATAAAGGAGCTTC
AAATGCAGGTCTATAAATAATGCACCGCATAGTTTTAAATATAAGGTTATTTCCTCGAAG 910        920        930        940        950        960
CACAAAAGGAATATTAGATGATACAGCGGATGGCTTTAGTGAAGAAAAAATAAAAAAGAT
GTGTTTTCCTTATAATCTACTATGTCGCCTACCGAAATCACTTCTTTTTATTTTTTCTA 970        980        990        1000       1010       1020
TATTCAATCTTTAAAAGACGGAACTTACTATCCTCAACCTGTACGAAGAATGTATATTGC
ATAAGTTAGAAATTTTCTGCCTTGAATGATAGGAGTTGGACATGCTTCTTACATATAACG 1030       1040       1050       1060       1070       1080
AAAAAAGAATTCTAAAAAGATGAGACCTTTAGGAATTCCAACTTTCACAGATAAATTGAT
TTTTTTCTTAAGATTTTTCTACTCTGGAAATCCTTAAGGTTGAAAGTGTCTATTTAACTA 1090       1100       1110       1120       1130       1140
CCAAGAAGCTGTGAGAATAATTCTTGAATCTATCTATGAACCGGTATTCGAAGATGTGTC
GGTTCTTCGACACTCTTATTAAGAACTTAGATAGATACTTGGCCATAAGCTTCTACACAG 1150       1160       1170       1180       1190       1200
TCACGGTTTTAGACCTCAACGAAGCTGTCACACAGCTTTGAAAACAATCAAAAGAGAGTT
AGTGCCAAAATCTGGAGTGGCTTCGACAGTGTGTCGAAACTTTTGTTAGTTTTCTCTCAA
```

MATCH TO FIG. 7C

*Fig. 7B*

MATCH TO FIG. 7B

```
        1210      1220      1230      1240      1250      1260
TGGCGGCGCAAGATGGTTTGTGGAGGGAGATATAAAAGGCTGCTTCGATAATATAGACCA
ACCGCCGCGTTCTACCAAACACCTCCCTCTATATTTTCCGACGAAGCTATTATATCTGGT 1270      1280      1290      1300      1310      1320
CGTTACACTCATTGGACTCATCAATCTTAAAATCAAAGATATGAAAATGAGCCAATTGAT
GCAATGTGAGTAACCTGAGTAGTTAGAATTTTAGTTTCTATACTTTTACTCGGTTAACTA 1330      1340      1350      1360      1370      1380
TTATAAATTTCTAAAAGCAGGTTATCTGGAAAACTGGCAGTATCACAAAACTTACAGCGG
AATATTTAAAGATTTTCGTCCAATAGACCTTTTGACCGTCATAGTGTTTTGAATGTCGCC 1390      1400      1410      1420      1430      1440
AACACCTCAAGGTGGAATTCTATCTCCTCTTTTGGCCAACATCTATCTTCATGAATTGGA
TTGTGGAGTTCCACCTTAAGATAGAGGAGAAAACCGGTTGTAGATAGAAGTACTTAACCT 1450      1460      1470      1480      1490      1500
TAAGTTTGTTTTACAACTCAAAATGAAGTTTGACCGAGAAAGTCCAGAAAGAATAACACC
ATTCAAACAAAATGTTGAGTTTTACTTCAAACTGGCTCTTTCAGGTCTTTCTTATTGTGG 1510      1520      1530      1540      1550      1560
TGAATATCGGGAACTTCACAATGAGATAAAAAGAATTTCTCACCGTCTCAAGAAGTTGGA
ACTTATAGCCCTTGAAGTGTTACTCTATTTTTCTTAAAGAGTGGCAGAGTTCTTCAACCT 1570      1580      1590      1600      1610      1620
GGGTGAAGAAAAAGCTAAAGTTCTTTTAGAATATCAAGAAAAACGTAAAAGATTACCCAC
CCCACTTCTTTTTCGATTTCAAGAAAATCTTATAGTTCTTTTTGCATTTTCTAATGGGTG 1630      1640      1650      1660      1670      1680
ACTCCCCTGTACCTCACAGACAAATAAAGTATTGAAATACGTCCGGTATGCGGACGACTT
TGAGGGGACATGGAGTGTCTGTTTATTTCATAACTTTATGCAGGCCATACGCCTGCTGAA 1690      1700      1710      1720      1730      1740
CATTATCTCTGTTAAAGGAAGCAAAGAGGACTGTCAATGGATAAAAGAACAATTAAAACT
GTAATAGAGACAATTTCCTTCGTTTCTCCTGACAGTTACCTATTTCTTGTTAATTTTGA 1750      1760      1770      1780      1790      1800
TTTTATTCATAACAAGCTAAAAATGGAATTGAGTGAAGAAAAAACACTCATCACACATAG
AAAATAAGTATTGTTCGATTTTTACCTTAACTCACTTCTTTTTTGTGAGTAGTGTGTATC
```

MATCH TO FIG. 7D

Fig. 7C

MATCH TO FIG. 7C

```
       1810       1820       1830       1840       1850       1860
CAGTCAACCCGCTCGTTTTCTGGGATATGATATACGAGTAAGGAGAAGTGGAACGATAAA
GTCAGTTGGGCGAGCAAAAGACCCTATACTATATGCTCATTCCTCTTCACCTTGCTATTT 1870       1880       1890       1900       1910       1920
ACGATCTGGTAAAGTCAAAAAGAGAACACTCAATGGGAGTGTAGAACTCCTTATTCCTCT
TGCTAGACCATTTCAGTTTTTCTCTTGTGAGTTACCCTCACATCTTGAGGAATAAGGAGA 1930       1940       1950       1960       1970       1980
TCAAGACAAAATTCGTCAATTTATTTTTGACAAGAAAATAGCTATCCAAAAGAAAGATAG
AGTTCTGTTTTAAGCAGTTAAATAAAAACTGTTCTTTTATCGATAGGTTTTCTTTCTATC 1990       2000       2010       2020       2030       2040
CTCATGGTTTCCAGTTCACAGGAAATATCTTATTCGTTCAACAGACTTAGAAATCATCAC
GAGTACCAAAGGTCAAGTGTCCTTTATAGAATAAGCAAGTTGTCTGAATCTTTAGTAGTG 2050       2060       2070       2080       2090       2100
AATTTATAATTCTGAATTAAGAGGGATTTGTAATTACTACGGTCTAGCAAGTAATTTTAA
TTAAATATTAAGACTTAATTCTCCCTAAACATTAATGATGCCAGATCGTTCATTAAAATT 2110       2120       2130       2140       2150       2160
CCAGCTCAATTATTTTGCTTATCTTATGGAATACAGCTGTCTAAAAACGATAGCCTCCAA
GGTCGAGTTAATAAAACGAATAGAATACCTTATGTCGACAGATTTTGCTATCGGAGGTT 2170       2180       2190       2200       2210       2220
ACATAAGGGAACACTTTCAAAAACCATTTCCATGTTTAAAGATGGAAGTGGTTCGTGGGG
TGTATTCCCTTGTGAAAGTTTTTGGTAAAGGTACAAATTTCTACCTTCACCAAGCACCCC 2230       2240       2250       2260       2270       2280
CATCCCGTATGAGATAAAGCAAGGTAAGCAGCGCCGTTATTTTGCAAATTTTAGTGAATG
GTAGGGCATACTCTATTTCGTTCCATTCGTCGCGGCAATAAAACGTTTAAAATCACTTAC 2290       2300       2310       2320       2330       2340
TAAATCCCCTTATCAATTTACGGATGAGATAAGTCAAGCTCCTGTATTGTATGGCTATGC
ATTTAGGGGAATAGTTAAATGCCTACTCTATTCAGTTCGAGGACATAACATACCGATACG 2350       2360       2370       2380       2390       2400
CCGGAATACTCTTGAAAACAGGTTAAAAGCTAAATGTTGTGAATTATGTGGAACATCTGA
GGCCTTATGAGAACTTTTGTCCAATTTTCGATTTACAACACTTAATACACCTTGTAGACT
```

MATCH TO FIG. 7E

*Fig. 7D*

MATCH TO FIG. 7D

```
         2410       2420       2430       2440       2450       2460
TGAAAATACTTCCTATGAAATTCACCATGTCAATAAGGTCAAAAATCTTAAAGGCAAAGA
ACTTTTATGAAGGATACTTTAAGTGGTACAGTTATTCCAGTTTTTAGAATTTCCGTTTCT 2470       2480       2490       2500       2510       2520
AAAATGGGAAATGGCAATGATAGCGAAACAACGTAAAACTCTTGTTGTATGCTTTCATTG
TTTTACCCTTTACCGTTACTATCGCTTTGTTGCATTTTGAGAACAACATACGAAAGTAAC
                                           →LtrA ORF
         2530       2540       2550        2560       2570       2580
TCATCGTCACGTGATTCATAAACACAAGTGAATTTTTACGAACGAACAATAACAGAGCCG
AGTAGCAGTGCACTAAGTATTTGTGTTCACTTAAAAATGCTTGCTTGTTATTGTCTCGGC 2590       2600       2610       2620       2630       2640
TATACTCCGAGAGGGGTACGTACGGTTCCCGAAGAGGGTGGTGCAAACCAGTCACAGTAA       LtrBI
ATATGAGGCTCTCCCCATGCATGCCAAGGGCTTCTCCCACCACGTTTGGTCAGTGTCATT 2650       2660       2670  2680       2690       2700
                                                                   LtrB.E2
TGTGAACAAGGCGGTACCTCCCTACTTCACCATATCATTTTTAATTCTACGAATCTTTAT
ACACTTGTTCCGCCATGGAGGGATGAAGTGGTATAGTAAAAATTAAGATGCTTAGAAATA 2710       2720       2730       2740       2750       2760
ACTGGCAAACAATTTGACTGGAAAGTCATTCCTAAAGAGAAAACAAAAAGCGGCAAAGCT
TGACCGTTTGTTAAACTGACCTTTCAGTAAGGATTTCTCTTTTGTTTTTCGCCGTTTCGA

… # METHODS FOR ANALYZING THE INSERTION CAPABILITIES OF MODIFIED GROUP II INTRONS

CROSS REFERENCE TO RELATED APPLICATIONS

This application is a continuation application of U.S. application Ser. No. 09/687,944, filed Oct. 13, 2000, now abandoned which claims priority to U.S. provisional application No. 60/159,724 filed Oct. 15, 1999.

This work was supported by NIH grant GM37949. The government has certain rights in this invention.

BACKGROUND OF THE INVENTION

Self-splicing RNAs are capable of catalyzing excision of their own introns in the absence of other protein or RNA factors. Self-splicing RNAs are classified into one of two groups, group I or group II, dependent on the reaction mechanism used to excise the intron. Group II introns excise themselves using a mechanism of action similar to that used in nuclear pre-mRNA splicing. In this mechanism, the 5' splice site is cleaved by attack from an adenosine nucleotide within the intron. The result is a lariat-like intermediate which is subsequently excised.

Group II introns encode ribonucleoprotein (RNP) particles, referred to hereinafter as "nucleotide integrases", that comprise an excised group II intron RNA and a group II intron-encoded protein which is bound to the excised group II intron RNA. Nucleotide integrases are molecular complexes capable of cleaving double-stranded DNA substrates at specific recognition sites and inserting nucleic acid molecules into the DNA substrate at the cleaved recognition site. Each nucleotide integrase cleaves substrate DNA and inserts nucleic acid molecules at specific recognition sites in the substrate DNA.

Methods of using nucleotide integrases are described in U.S. Pat. No. 5,698,421 and U.S. Pat. No. 6,027,895, both of which are specifically incorporated herein by reference. The process of cleaving the DNA substrate and inserting nucleic acid molecules involves base pairing of the group II intron RNA of the nucleotide integrase to a specific region of the DNA substrate. Additional interactions occur between the intron-encoded protein and regions in the DNA substrate flanking the recognition site. In general, the method comprises the steps of: providing a nucleotide integrase comprising a group II intron RNA having two sequences, EBS1 and EBS2, that are capable of hybridizing with two intron RNA-binding sequences, IBS1 and IBS2, on the top strand of the DNA substrate, and a group II intron-encoded protein that binds to a first sequence element and to a second sequence element in the recognition site of the substrate; and reacting the nucleotide integrase with the double-stranded DNA substrate for a time and at a temperature sufficient to permit the nucleotide integrase to cleave both strands of the DNA substrate and to insert the group II intron RNA into the cleavage site of the top strand. The first sequence element of the recognition site is upstream of the putative cleavage site, the IBS 1 sequence and the IBS 2 sequence. The first sequence element comprises from about 10 to about 12 pairs of nucleotides. The second sequence element of the recognition site is downstream of the putative cleavage site and comprises from about 10 to about 12 nucleotides.

As denoted herein, nucleotides that are located upstream of the cleavage site have a (−) position relative to the cleavage site, and nucleotides that are located downstream of the cleavage site have a (+) position relative to the cleavage site. Thus, in the above-described method, the cleavage site is located between nucleotides −1 and +1 on the top strand of the double-stranded DNA substrate. The IBS1 sequence and the IBS2 sequence lie in a region of the recognition site which extends from about position −1 to about position −14 relative to the cleavage site.

EBS1 is located in domain I of the group II intron RNA and comprises from about 5 to 7 nucleotides that are capable of hybridizing to the nucleotides of the IBS1 sequence of the substrate. EBS2 is located in domain I of the group II intron RNA upstream of EBS1 and comprises from about 5 to 7 nucleotides that are capable of hybridizing to the nucleotides of IBS2 sequence of the substrate. In order to cleave the substrate efficiently, it is referred that the nucleotide or sequence δ, which immediately precedes the first nucleotide of EBS1 of the group II intron RNA, be complementary to the nucleotides at +1 in the top strand of the substrate.

Examples of nucleotide integrases which may be used to catalyze the cleavage of double-stranded DNA molecules are the aI2 nucleotide integrase, the aI1 nucleotide integrase, and the ltrA nucleotide integrase. The aI2 integrase is an isolated RNP particle that comprises a wild-type or modified group II intron RNA of the second intron of the *S. cerevisiae* mitochondrial COX1 gene, hereinafter referred to as the "aI2 intron" RNA, bound to a wild-type or modified aI2 intron encoded-protein. EBS1 of the aI2 intron RNA comprises 6 nucleotides and is located at position 2985-2990 of the wild-type sequence. EBS1 of the wild-type aI2 intron RNA has the sequence 5'-AGAAGA. EBS2 of the aI2 intron RNA comprises 6 nucleotides and is located at positions 2935-2940. EBS2 of the wild-type aI2 intron RNA has the sequence 5'-UCAUUA.

The aI1 nucleotide integrase is an isolated RNP particle that comprises an excised, wild-type or modified excised group II intron RNA of the first intron of the *S. cerevisiae* mitochondrial COX1 gene, hereinafter referred to as the "aI1 intron" RNA, and a wild-type or modified aI1 intron-encoded protein. EBS1 of the aI1 intron RNA comprises 6 to 7 nucleotides and is located at position 426-431. EBS1 of the wild-type aI1 intron RNA has the sequence 5'-CGUUGA. EBS2 of the aI1 intron RNA comprises 5 to 6 nucleotides and is located at positions 376-381. EBS2 of the wild-type aI1 intron RNA and has the sequence 5'-ACAAUU.

The ltrA nucleotide integrase comprises an excised, wild-type or modified excised group L1.LtrB group II intron RNA of the *Lactococcus lactis* ltrB gene, hereinafter referred to as the "L1.ltrB intron" RNA, and a wild-type or modified L1.ltrB intron-encoded protein, hereinafter referred to as the ltrA protein. The sequence of the L1.ltrB intron is shown in FIG. 7. The EBS1 of the L1.ltrB intron RNA comprises 7 nucleotides and is located at positions 457 to 463. The EBS1 sequence of the wild-type L1.ltrB intron RNA has the sequence 5'-GUUGUGG. The EBS2 of the L1.ltrB intron RNA comprises 6 nucleotides and is located at positions 401 to and including 406. The EBS2 sequence of the wild-type L1.ltrB intron RNA has the Sequence 5'AUGUGU.

In recent years, methods have been developed for preparing nucleotide integrases whose excised group II RNAs have a wild-type sequence and nucleotide integrases whose excised group II RNAs have a modified sequence. Such methods are described in U.S. Pat. No. 5,804,418, which is specifically incorporated herein by reference. The modified nucleotide integrases can catalyze the cleavage of DNA substrates and the insertion of nucleic acid molecules at new recognition sites in the DNA substrate. Because the recognition site of the DNA substrate is recognized, in part, through base pairing with the excised group II intron RNA of the nucleotide integrase, it is possible to control the site of nucleic acid insertion within the DNA substrate. This is done by modifying the EBS 1 sequence, the EBS 2 sequence or the δ sequence, or combinations thereof. Such modified group II introns produce nucleotide integrases that can cleave DNA substrates and insert nucleic acid molecules at new recognition sites in the genome.

Modified nucleotide integrases are useful analytical tools for determining the presence and location of a particular target sequence in a DNA substrate. Modified nucleotide integrases are also useful tools for rendering certain genes within DNA substrates nonfunctional. Modified nucleotide integrases are also useful tools for inserting a nucleic acid into the cleavage site, thus changing the characteristics of the cellular DNA and RNA and protein molecules encoded by the cellular DNA.

Accordingly, analytical systems and methods which can be used to determine, first, whether or not a modified nucleotide integrase functions to cleave substrate DNA and insert nucleic acid molecules and, second, to analyze the recognition site where this occurs are desirable.

SUMMARY OF THE INVENTION

The present invention provides a system and methods for analyzing nucleotide integrases, particularly those nucleotide integrases whose excised group II intron RNAs comprise a modified EBS1 sequence, a modified EBS2 sequence, a modified delta sequence, or any combination thereof. As used herein, a "modified" EBS or δ sequence is a sequence which is different from the wild-type EBS or delta sequence, respectively, of the group II intron RNA. Such systems and methods are useful for determining whether the modified nucleotide integrases are able to catalyze the cleavage of a particular DNA substrate recognition site.

The system for analyzing nucleotide integrases comprises a donor plasmid comprising a group II intron DNA sequence having a modified EBS1 sequence, a modified EBS2 sequence, a modified δ sequence or any combination thereof, and a recipient plasmid comprising the particular target DNA recognition site into which the group II intron will insert. The modified group II intron DNA sequence within the donor plasmid preferably lacks a portion, preferably from about 50% to about 90% of domain IV (the group II intron typically has six domains), and further comprises a promoter, which is preferably located in the region that has been deleted from domain IV of the group II intron. The recipient plasmid further comprises a promoterless reporter gene, which is preferably a gene encoding a selectable marker, downstream from the target sequence. In one embodiment, the donor plasmid further comprises a sequence which encodes a group II intron-encoded protein. The protein-encoding sequence is located upstream or downstream of the group II intron DNA sequence. In another embodiment, the recipient plasmid comprises a sequence encoding a group II intron-encoded protein.

The method comprises transforming a cell, preferably a bacterial cell, more preferably, *Escherichia coli*, with both the donor plasmid and the recipient plasmid, and assaying the co-transformed cells for expression of the reporter gene. Expression of the reporter gene is indicative of cleavage of the target recognition site and insertion of the modified intron into the cleaved recognition site. Preferably, expression of the reporter gene is assayed by culturing the co-transformed cells in the presence of a selectable agent, such as, for example, an antibiotic. Preferably, the method further comprises the step of isolating plasmid DNA from the co-transformed cells and analyzing the plasmid DNA to confirm that the group II intron has been inserted into the target recognition site.

The present invention also provides a method for simultaneously analyzing two or more modified nucleotide integrases. The method comprises the steps of: (a) providing a plasmid pool comprising a first donor plasmid comprising a first modified group II intron DNA sequence and a second donor plasmid comprising a second modified group II intron DNA sequence, wherein the first modified sequence is different from the second modified sequence, and wherein the modified group II intron DNA sequence in each donor plasmid preferably further comprises a promoter and lacks a portion, preferably from 50% to 90% of domain IV, and wherein each donor plasmid further comprises a sequence encoding the protein normally encoded by the group II intron, said protein-encoding sequence being upstream or downstream from the group II intron DNA sequence; (b) providing a recipient plasmid comprising a target DNA recognition site and a promoterless reporter gene downstream from said target DNA recognition sequence; (c) transforming cells with said recipient plasmid and said first donor plasmid; (d) transforming cells with said second donor plasmid and said recipient plasmid; (e) assaying the transformed cells for expression of the reporter gene to obtain cells which comprise a target DNA recognition sequence into which the first modified group II intron DNA sequence or the second modified group II intron DNA sequence have been inserted into the target DNA recognition sequence of said cells; and (f) determining the sequences of the modified group II introns that have been inserted into the target sequence of said cells.

Such analytical method is useful for determining whether one or both of the modified nucleotide integrases that are produced within the co-transformed cells are capable of catalyzing cleavage of the target DNA recognition sequence. In addition, such analytical method is useful to determine whether one modified nucleotide integrase has a higher insertion frequency into the target DNA recognition sequence than the other modified nucleotide integrase. Such information is useful in selecting nucleotide integrases which are best suited to catalyze cleavage of the target DNA recognition sequence. Moreover, the donor plasmid pool can contain a library of plasmids that comprise a plurality of diverse modified group II intron DNA sequences such that thousands or millions of different modified group II introns can be analyzed simultaneously using the present method.

The present invention also relates to a DNA or RNA construct comprising a modified group II intron sequence which lacks a portion of domain IV and which comprises a modified EBS1 sequence, or a modified EBS2 sequence, or a combination of both a modified EBS1 sequence and a modified EBS2 sequence. The construct also comprises a promoter operatively linked to the modified intron sequence. Preferably, the construct further comprises a sequence encoding a group II intron-encoded protein, said protein encoding sequence being upstream or downstream of the modified group II intron DNA sequence and being operatively linked to a promoter.

The present invention also relates to methods of preparing a library of donor plasmids containing a plurality of diverse modified group II intron DNA sequences and a method of using such library to randomly mutagenize DNA molecules.

The present method could also be applied to study of transposition and targeting of other transposable elements.

BRIEF DESCRIPTION OF THE FIGURES

FIGS. 3A and B. Base-pairing requirements for different positions of the DNA target site. A mobility assay was performed with the wild-type donor plasmid pACD-ORF+ORF2 and a recipient plasmid pool in which DNA target site positions between −30 and +15 were partially randomized ("doped") to contain 70% of the wild-type nucleotide and 10% each of the three mutant nucleotides. The number of potential base pairs with the intron RNA was compared in active target sites (black bars) and the original recipient pool (white bars). (A) Percentage of target sites having a potential base pair with the intron RNA at each position between −13 and +4. (B) Percentage of target sites having the indicated number of potential base pairs over the indicated interval. Selection for base pairing in the active target sites is evident at all positions except −7.

FIG. 7. The nucleotide sequence of a 2.8 kb HindIII fragment includes the L1.ltrB intron DNA sequence and portions of the nucleotide sequence of the flanking exons ltrBE1 and ltrBE2 (SEQ ID NO: 11).

DETAILED DESCRIPTION OF THE INVENTION

I. Definitions

Figure 1A:
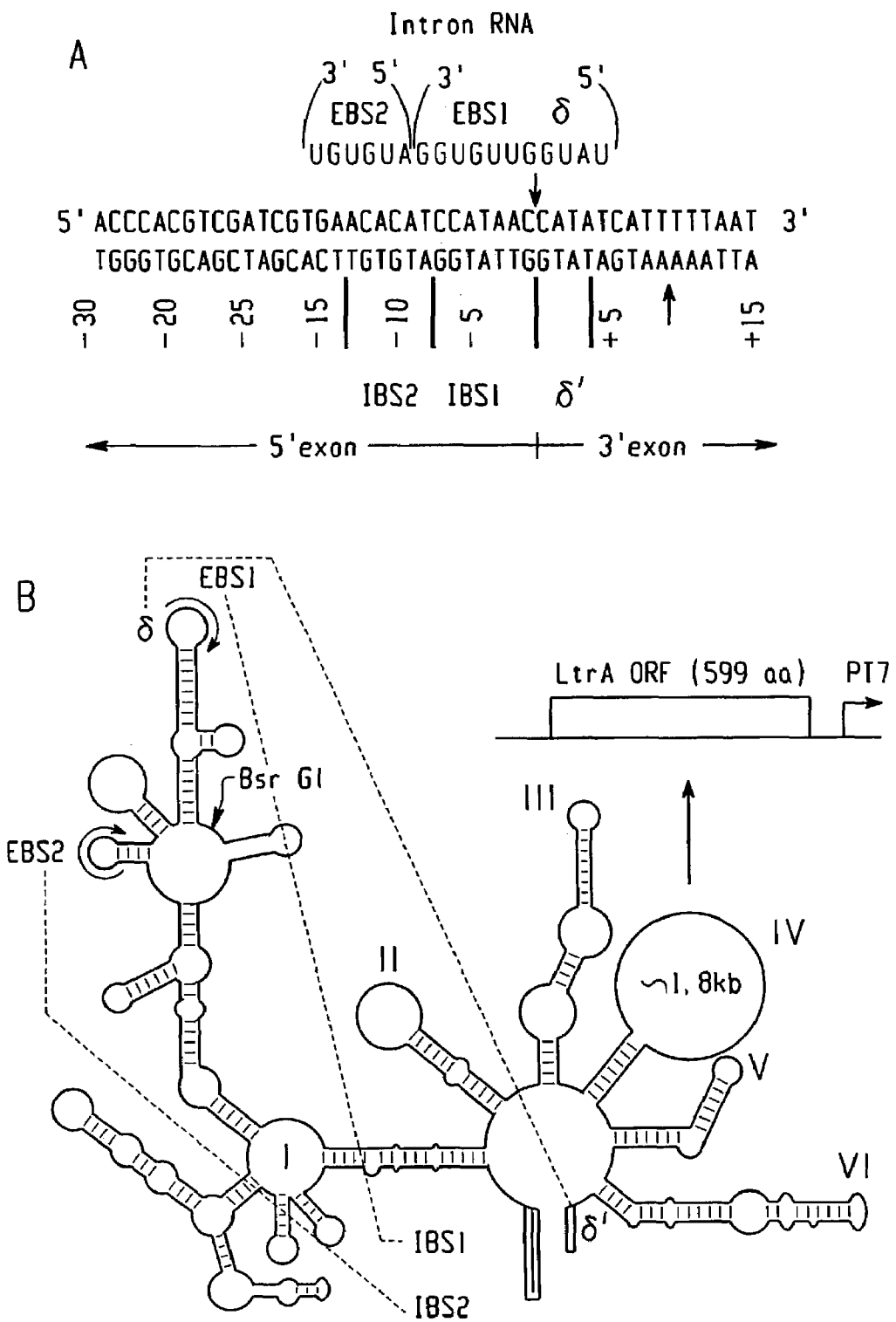
FIG. 1. *E. coli* genetic assay based on the L1.LtrB intron for analyzing group II intron/DNA target site interactions. (A) Natural L1.LtrB DNA target sequence from position −30 to +15 and base-pairing interactions with the intron RNA. Sequence elements IBS2 and IBS1 in the 5' exon and δ' in the 3' exon of the DNA target are recognized primarily by base pairing with sequence elements EBS2, EBS1 (SEQ ID NO: 12) and δ located in domain I of the intron RNA. The intron-insertion site in the top (sense) strand (SEQ ID NO: 13) and the endonuclease cleavage site in the bottom (antisense) strand are indicated by arrows. (B) Schematic of the L1.LtrB intron showing base-pairing interactions EBS1-IBS1, EBS2-IBS2, and δ-δ' between the intron and flanking exons. The inset shows the location of the LtrA ORF and the T7 promoter introduced into intron domain IV in donor plasmids. (C) Genetic assay. The donor plasmid pACD-LtrB is a Cam$^R$ pACYC184-derivative containing the full-length L1.LtrB intron and flanking exons, with a phage T7 promoter inserted downstream of the LtrA ORF in intron domain IV. The intron and flanking exon sequences (E1 and E2) are cloned behind a T7lac promoter, and *E. coli* rrnB T1 and T2 transcription terminators are positioned downstream of the intron. The recipient pUCR-LtrB/Tet is a compatible Amp$^R$ plasmid with an L1.LtrB target sequence (ligated ltrB exons E1-E2) cloned upstream of a promoterless tet$^R$ gene. An *E. coli* rrnB T1 transcription terminator, which terminates both *E. coli* and T7 RNA polymerase, is inserted upstream of the target site, and an rrnB T2 terminator, which terminates *E. coli* but not T7 RNA polymerase, is inserted between the target site and the tet$^R$ gene. A phage T7 TΦ terminator is inserted downstream of the tet$^R$ gene to terminate T7 RNA polymerase. Movement of the intron carrying the phage T7 promoter into the DNA target site activates expression of the tet$^R$ gene. (D) Mobility assay using pACD-ΔORF+ORF1. This plasmid has a deletion in the loop of intron domain IV, which removes most of the LtrA ORF, and the LtrA protein is expressed separately from a position downstream of the 3' exon. This configuration gives higher mobility frequencies approaching 100%.

"Group II intron DNA," as used herein, is a specific type of DNA present in bacteria and in organelles, particularly the mitochondria of fungi, yeast and plants and the chloroplast of plants. The group II intron RNA molecules, that is, the RNA molecules which are encoded by the group II introns, share a similar secondary and tertiary structure. The group II intron RNA molecules typically have six domains. Domain IV of the group II intron RNA contains the nucleotide sequence which encodes the "group II intron-encoded protein."

"Excised group II intron RNA," as used herein, refers to an RNA that is either an in vitro or in vivo transcript of the group II intron DNA that lacks flanking exon sequences. The excised group II intron RNA is obtained from wild-type organisms, or mutated organisms, by in vivo transcription and splicing, or by in vitro transcription and splicing from the transcript of a modified or unmodified group II intron.

"Group II intron encoded protein," as used herein, is a protein encoded by a group II intron open reading frame. The group II intron-encoded protein comprises an X domain and a reverse transcriptase domain. The X domain of the protein has a maturase activity. In some cases, the proteins also comprise a Zn domain having $Zn^{2+}$ finger-like motifs. As used herein, group II intron-encoded proteins also encompass modified group II intron-encoded proteins that have additional or altered amino acids at the N terminus, or C terminus, or alterations in the internal regions of the protein, as well as wild-type group II intron-encoded proteins. It is believed that the group II intron-encoded protein is bound mainly to the 5' and 3' ends of domain IV of the group II intron RNA.

"Modified," as used herein, refers to DNA, RNA or proteins which differ from the wild-type form of the DNA, RNA, or protein. In the case of DNA or RNA, modified refers to one or more of substitutions, additions or deletions of nucleotides in the DNA or RNA sequence, such that the modified sequence is different from the normal, wild-type sequence. Modified can refer to substitutions, additions or deletions of nucleotides in a sequence within DNA or RNA that does not encode a protein, such as for example, one or more of the EBS1, EBS2 and δ regions of the Group II intron. Modified can also refer to substitutions, additions or deletions of nucleotides, as compared to normal wild-type, within a protein-encoding sequence of the DNA or RNA. The protein encoded by such a modified protein-encoding DNA or RNA sequence could itself be modified in that it could have one or more of substitutions, additions or deletions of amino acids within its protein sequence as compared to the normal, wild-type sequence of the protein.

"Nucleotide integrase," as used herein, refers to an RNP particle that functions as an endonuclease that cleaves DNA and that is also able to insert a nucleic acid molecule into the cleavage site of the DNA substrate. Such RNP particles comprise a group II intron-encoded protein which is bound to an excised group II intron RNA whose sequence is identical to a group II intron RNA that is found in nature, i.e. a wild-type group II intron RNA, or an excised group II RNA whose sequence is different from a group II intron RNA that is found in nature, i.e. a modified, excised group II intron RNA molecule. Modified excised group II intron RNA molecules, include, for example, group II intron RNA molecules that have nucleotide base changes or additional nucleotides in the internal loop regions of the group II intron RNA, preferably the internal loop region of domain IV, and group II intron RNA molecules that have nucleotide base changes in the hybridizing regions of domain I. Nucleotide integrases in which the group II intron RNA has nucleotide base changes in the hybridizing region, as compared to the wild type, typically have altered specificity for the DNA substrate of the wild-type nucleotide integrase.

"DNA recognition sites," as used herein, refer to the sequence of nucleotide bases within the DNA substrate which are recognized by the nucleotide integrase, or components thereof, as signals to cleave the DNA substrate and then insert nucleic acid molecules into the substrate. DNA recognition sites can also be referred to as "targets" since these are sites into which nucleic acid molecules are inserted.

"DNA substrate," as used herein, means the DNA molecule containing DNA recognition sites which are cleaved by the nucleotide integrases and into which nucleic acid molecules are inserted.

"Insertion frequency," as used herein, means the ratio of recipient plasmids having a group II intron DNA sequence inserted into the target DNA recognition site thereof, to the total number of recipient plasmids.

"Selection frequency," as used herein, means the percentage of co-transformed cells that express the reporter gene.

"Transformation," as used herein, means introduction of nucleic acid molecules, preferably DNA, into cells and maintenance of the cells under conditions which allow for transcription of the group II intron and expression of proteins encoded by the group II intron. Herein, transformation includes, but is not inclusive of, introduction of DNA into cells by methods such as calcium chloride or other chemical treatment of cells, electroporation, liposomes, and viral or other vectors. Transformation can refer to introduction of DNA into bacterial, fungal, animal or plant cells.

"Promoter," as used herein, refers to sequences in DNA where transcription by an RNA polymerase is specifically initiated. Transcriptional promoters may comprise one or more of a number of different sequence elements as follows: 1) sequence elements present at the site of transcription initiation; 2) sequence elements present upstream of the transcription initiation site and; 3) sequence elements downstream of the transcription initiation site. The individual sequence elements function as sites on the DNA where RNA polymerases, and transcription factors that facilitate positioning of RNA polymerases on the DNA, bind.

"Heterologous gene," as used herein, refers to nucleotide sequences not normally encoded by a group II intron, that are inserted into a group II intron, preferably using recombinant DNA techniques. Such heterologous genes can then be inserted into the DNA substrate, at or near the DNA recognition site, as part of the process by which the group II intron encoding the heterologous gene, is inserted into the DNA substrate.

"Localization signals," as used herein, refer to amino acid or peptide sequences that are recognized intracellularly and selectively transported to specific locations within the cell. For example, localization signals exist, and are known in the art, that are responsible for transport to the nucleus, mitochondria and chloroplasts. By incorporating localization signals within other cellular proteins, it is possible to direct the entire protein to the intracellular location to which the specific peptide localization signal is transported. This can be done, preferably using recombinant DNA methodology, by fusing the DNA sequence encoding a specific localization signal to a gene encoding a protein that one wants to localize to a specific site in the cell.

"Purification tag," as used herein, refers to an amino acid or peptide sequence that, when present inside a cell together with cellular proteins, can easily be purified away from the other cellular proteins because the peptide sequence can readily be recognized. Recognition of these peptides normally depends on specific binding of the peptide with a specific reagent, such as for example, an antibody. Another example is the high affinity of a peptide containing six contiguous histidine amino acids to bind to nickel. By incorporating such purification tags within other proteins (i.e., a fusion protein), it is possible to rapidly purify such proteins based on the high affinity of the purification tag with the specific reagent This can be done, preferably using recombinant DNA methodology, by fusing the DNA sequence encoding a purification tag peptide to a gene encoding a protein that one wants to rapidly purify when expressed in a cell. If the fusion protein is able to bind other molecules within the cell, an RNA molecule for example, it may be possible to purify both fusion protein and bound RNA based on affinity of the purification tag within the fusion protein, with the reagent.

"Detection Tag" as used herein refers to an amino acid or peptide sequence that when linked to a group II intron encoded protein allows detection of cells expressing such protein. Examples include GFP and lacZ.

II. Methods of Analyzing Modified Nucleotide Integrases

The present invention provides systems and methods for analyzing one or a plurality of nucleotide integrases. The methods comprise transforming host cells with a donor plasmid or a pool of donor plasmids, each of which contains a modified group II intron DNA sequence, and a recipient plasmid which contains a target DNA recognition site; and assaying for insertion of the modified group II intron DNA sequence into the target DNA recognition site of the recipient plasmid. The present invention also relates to DNA constructs and RNA constructs useful for preparing the donor plasmid. Such constructs are also useful for reacting nucleotide integrases with DNA substrates intracellularly.

A. DNA Construct and Donor Plasmid

The DNA construct comprises a modified group II intron DNA sequence operatively linked to a promoter. The modified group II intron DNA sequence has a modified EBS1 sequence, or a modified EBS2 sequence, a modified δ region, or any combination thereof The modified group II intron DNA sequence preferably lacks a portion of domain IV, preferably from about 50% to about 90%, more preferably from about 65% to about 90%, most preferably from about 80% to about 90% of the loop region of domain IV, while retaining a plurality of nucleotides at the 5' end and the 3' end of domain IV. Preferably, about 95 to about 200 nucleotides are retained at the 5' end and about 25 to about 150 nucleotides are retained the 3' end of domain IV. As a result of the deletion, the group II intron DNA sequence does not encode a full-length protein. Depending upon the intron and the size of the deletion, the modified intron either comprises no open reading frame or a disrupted open reading frame which encodes a truncated protein. For the L1.LtrB intron, whose domain IV is about 1.9 kilobases in size, good results are obtained when nucleotides at intron position 691 (from the beginning of the intron) through intron position 2286 are deleted from the intron. For the L1.ltrB intron, good results are obtained when 95 to 164 nucleotides are retained at the 5' end and when 28 to 108 nucleotides are retained at the 3' end of the intron domain IV. In one embodiment, the DNA construct further comprises a sequence which encodes the protein that is normally encoded by the group II intron. The protein-encoding sequence is located either upstream or downstream of the group II intron sequence and is operatively linked to a promoter. Thus, the construct can contain a single promoter which drives transcription of the intron and expression of the protein. Alternatively, the construct can contain two promoters, one of which drives transcription of the intron, and one of which drives expression of the protein. Suitable promoters include, but are not limited to, tissue-specific promoters, constitutive promoters such as CMV, and inducible promoters such as lac, tac, T7 lac, and lac UV5. Preferably, the construct further comprises sequences which flank the intron and allow splicing of the group II intron RNA from the intron transcript. Such sequences are complementary to the EBS1 and EBS2 sequences of the modified group II intron. Optionally, the group II intron further comprises a heterologous sequence in domain IV. In one embodiment, the heterologous sequence is a promoter. In another embodiment, the heterologous sequence is a sequence of from about 2 base pairs to 1.4 kilobase pairs. Optionally, the construct further comprises a sequence encoding an RNA polymerase, which is specific for the promoter that is operatively linked to the group II intron DNA sequence, or the protein-encoding sequence. The RNA polymerase-encoding sequence is operatively linked to a constitutive, or inducible, or tissue specific promoter. Preferably, the polymerase-encoding sequence is not transcribed in the same direction as the group II intron DNA sequence and the group II intron protein-encoding sequence.

For use in the present method, the above DNA construct, preferably, is inserted into a plasmid or an expression vector. Such plasmids or expression vectors may be used to transform bacterial, mammalian, or any other types of cells. DNA plasmids are commonly used to transform bacterial cells, but can also be used to transform other cells, such as for example, cells derived from mammalian animals. To transform mammalian cells, the DNA construct is preferably inserted into viral or other vectors, such as for example, an SV40-derived expression vector, an adenovirus-derived expression vector, an adeno-associated virus vector, a poxvirus-derived viral vector or a retrovirus-derived viral vector.

In one embodiment there are two donor plasmids, one of which contains the modified group II intron DNA sequence and one of which contains the protein-encoding sequence. In another embodiment, the donor plasmid comprises both the group II intron DNA sequence and protein encoding sequence. The group II intron sequence in the donor plasmid further comprises a promoter for driving expression of reporter genes that are located in the recipient plasmid, once insertion of the group II intron DNA sequence into the target sequence occurs (hereinafter referred to as the "reporter gene promoter"). Preferably, the reporter gene promoter is located within the remaining portion of domain IV of the intron. For the L1.ltrB intron, good results are obtained when the reporter gene promoter is located upstream of intron position 2366 and downstream of intron position 621. Suitable reporter gene promoters include constitutive promoters and inducible promoters. Preferred promoters are those which are very strong and used very specifically by a very active and processive RNA polymerase, such as for example, the phage T3 promoter and the phage T7[1] promoter. Preferably, the donor plasmid further comprises a selectable marker gene which allows selection of cells that have been transformed with the donor plasmid. Preferably, the donor plasmid further comprises an origin of replication.

[1] As described in Studier et al., Methods in Enzymology, (1990) 185:60-89, phage T7 promoters are recognized and used by phage T7 RNA polymerase, which is highly selective for specific promoters that are rarely found in any DNA other than phage T7 DNA. No T7 promoters are known to be present in the chromosomal DNA of *E. coli*. In addition, T7 RNA polymerase is a very processive enzyme, i.e., there are very few transcription terminators that are able to block transcription by the T7 polymerase. Moreover, T7 RNA polymerase is a very active enzyme which trancribes DNA about 5 times faster than *E. coli* RNA polymerase.

B. Recipient Plasmids

The recipient plasmid comprises a target DNA recognition site for analyzing the endonuclease activity of the RNP particle that comprises the excised group II intron RNA and the protein encoded by the DNA construct (nucleotide integrase). The recipient plasmid further comprises a promoterless reporter gene, downstream from the target sequence. Preferably, the reporter gene encodes a selectable gene, such as for example, a tetracycline-resistance gene, which allows selection of transformed cells comprising a recipient plasmid whose target DNA recognition site has the modified group II intron DNA sequence inserted therein. Preferably, the recipient plasmid further comprises a distinct selectable marker gene for allowing selection of cells that have been transformed with the recipient plasmid. Such a selectable marker gene is operatively linked to a promoter, preferably a constitutive promoter, and is in the opposite orientation of the promoterless reporter gene. Preferably, the recipient plasmid further comprises a first transcription terminator between the target sequence and the promoterless reporter gene. The first transcription terminator is selected to prevent non-specific transcription of the promoterless reporter gene from cryptic promoters in the target sequence or further upstream of the target sequence and to allow transcription of the promoterless reporter gene upon integration of the group II intron DNA sequence into the target DNA recognition site. Good results have been obtained with the phage T7 Te terminator and the *E. coli* rrnBT2 terminator, both of which allow T7 RNA polymerase to transcribe through and prevent *E. coli* RNA polymerase transcription. The *E. coli* rrnBT2 terminator terminates *E. coli* RNA polymerase more efficiently, and is, thus, more preferred. More preferably, the recipient plasmid further comprises a second transcription terminator upstream of the target sequence for preventing any non-specific transcription of the reporter gene from a promoter upstream of the target sequence. Good results have been obtained using an *E. coli* rrnB T1 transcription terminator which terminates both *E. coli* and phage T7 RNA polymerase transcription. Preferably, the recipient plasmid further comprises a third transcription terminator downstream of the reporter gene to terminate transcription from the reporter gene promoter. Good results have been obtained using the phage T7 Tø terminator to terminate phage T7 RNA polymerase transcription. Preferably, the recipient plasmid comprises a replication origin which is different from the replication origin of the donor plasmid.

C. Host Cells

In the present method, the recipient plasmid and donor plasmid are introduced into host cells which comprise a gene encoding an RNA polymerase which, preferably, is specific for the promoter that is located in the modified group II intron DNA sequence of the donor plasmid (referred to hereinafter as the "control polymerase"). For example, in cases where the group II) intron contains a phage T7 promoter or a phage T3 promoter, the host cell comprises a gene which encodes the T7 RNA polymerase or the T3 RNA polymerase, respectively. Preferably, the control polymerase gene is operatively linked to an inducible promoter such as for example, lacUV5 promoter, lac or tac promoters. Suitable host cells are bacterial, fungal, plant or animal cells. Preferably, the host cell is a bacterium such as, for example, *E. coli*.

D. Methods of Assaying for the Insertion of the Modified Group II Intron into the Target Sequence The recipient plasmid and donor plasmids are introduced into the host cells either concurrently or sequentially. The cells are maintained in medium under conditions which allow for transcription of the RNA encoded by the group II intron sequence, expression of the group II intron-encoded protein, and formation of the nucleotide integrase which comprises these macromolecules. The transformed cells are monitored for expression of the promoterless reporter gene. Expression of the promoterless reporter gene occurs when the modified group II intron DNA sequence is inserted into the target DNA recognition site of the recipient plasmid. To confirm that expression of the promoterless reporter gene is due to insertion of group II intron DNA sequence into the target DNA recognition site, plasmid DNA is isolated from the selected cells and the sequence of the target sequence analyzed by restriction enzyme analysis and DNA sequencing analysis. Optionally, prior to isolation of the plasmid DNA, the selected cells are analyzed by polymerase chain reaction (PCR) to determine whether the target sequence has been disrupted by insertion of the group II intron. Such analysis provides information about the sequence, particularly the EBS1 and EBS2 sequences of the inserted group II intron DNA sequence, and the location of the insertion site. Retransformation of the isolated plasmid DNA into host cell, followed with plating of the host cells on selection medium provides information about the insertion frequency of the group II intron.

III. Method of Preparing a Donor Plasmid Library

A library of donor plasmids is made using a two-step PCR procedure. The library comprises a plurality of plasmids whose modified group II intron DNA sequences comprise randomized EBS1 sequences and randomized EBS2 sequences. In the first step, a template is employed which comprises the full-length group II intron DNA sequence, which is preferably flanked by from 1 to 26 nucleotides of the 5' exon (i.e. the exon that is normally linked to the 5' end of the group II intron). In the first PCR step, two sets of primer pairs are used. The sense primers of the first set comprise, in the following order: a first region having a sequence which is complementary to a 5' exon sequence which is upstream of the IBS sequences, a second region comprising from 2 to 13 randomized nucleotide positions, and a third region having a sequence which is complementary to an intron sequence located downstream from the 5' end of the intron and upstream of the EBS2 sequence. The antisense primers of the first set comprise a sequence which is complementary to a downstream intron sequence, said downstream intron sequence being located upstream of the EBS2 sequence. The sense primers of the second set comprise, in the following order: a first region which is complementary to an intron sequence upstream of the EBS2 sequence, a second region comprising from 2 to about 6 randomized nucleotides in the region of the EBS2 sequence, and a third region having a sequence which is complementary to an intron sequence that is downstream of the EBS2 sequence. The antisense primers of the second set comprise in the following order: a first region having a sequence which is complementary to an intron sequence which is downstream of the EBS1 sequence, a second region comprising from 2 to 7 randomized nucleotide positions, and a third region having a sequence which is complementary to an intron sequence upstream of the δ and EBS1 sequence. The PCR products made using the first set of primers comprise a 3' sequence which partially overlaps with the 5' sequence of the PCR products made using the second set of primers. The purified PCR products of the first PCR step are used as templates in the second PCR step. The primers used in the second PCR step are the sense primers of the first set and the antisense primers from the second set, in the first PCR step. The primers used in the second PCR step, preferably, also comprise unique restriction enzyme sites at the 5' and 3' ends thereof. The DNA fragments that are produced as a result of the second PCR step are digested with the respective restriction enzymes and cloned into plasmids comprising the corresponding group II intron DNA sequence which has been modified to contain the same restriction enzyme sites. This procedure provides a plurality of plasmids comprising a plurality of group II intron DNA sequences having diverse EBS1 sequences and EBS2 sequences, and further comprising a plurality of diverse sequences upstream of the EBS1 sequences. Standard techniques are then used to amplify the library.

Such libraries encode group II introns with the capability to insert into many different target DNA recognition sites. When group II introns insert themselves into DNA, the target DNA recognition site is disrupted due to the insertion. Such disruption of a target recognition site can result in a genetic mutation in the cell in which the intron has inserted. Therefore, libraries containing a plurality of group II introns can be used to mutagenize cells. For example, introduction of said libraries into cells will result in integration of the group II introns into many different genomic sequences of those cells, potentially disrupting many different genes contained within the cells. Individual cells may be isolated from the pool of intron-containing cells to isolate cell clones that have intron insertions into specific genes. Such mutagenesis could be used in bacterial, fungal, plant, mammalian and other types of cells.

Mobile group II introns are site-specific retrotransposons. Intron mobility requires the intron-encoded DNA endonuclease, which is an RNP complex, containing both the spliced intron RNA and the intron-encoded protein. The intron-encoded DNA endonuclease uses both the intron RNA and the intron-encoded protein to recognize specific target sequence in a double-stranded DNA. The intron RNA recognizes 13-16 nt of the target DNA through base pairing interactions, allowing the endonuclease's specificity to be changed predictably. Thus, randomization of the target recognition sequences in the intron RNA will generate a pool of mobile introns with diverse specificities. This kind of intron library could be used as a mutagen. The advantage of using mobile group II intron as a mutagen is that a disfunctioned gene will be concomitantly tagged with a group II intron. In addition, in a diploid organism, both alleles could be knocked out simultaneously.

For mutagenesis, the donor intron library (the huge pool of donor intron constructs) with randomized IBS and EBS sequences will be transformed or transfected into a pool of cells. Following induction for intron transposition, mutants could be generated due to intron transposition. Since a gene knocked out using this method will be tagged with a group II intron, the mutated gene will be easily identified.

IV. Using the Donor DNA Construct to Prepare Modified Nucleotide Integrases

Modified nucleotide integrases can be isolated from cells transformed with a donor DNA construct encoding a modified group II intron and a group II intron-encoded protein. To improve isolation, the DNA construct may be engineered such that the group II intron-encoded protein is linked to a purification tag. Such particles are reacted with the DNA substrate extracellularly by incubating the particles with the DNA substrate in a buffer comprising magnesium ions. Such particles can also be reacted with the DNA substrate intracellularly by introducing the particles into a host cell comprising the DNA substrate. Methods of introducing such particles into the cell include, but are not limited to, microinjection and the use of liposomes.

Alternatively, the nucleotide integrase may be reacted with the DNA substrate intracellularly by introducing the donor DNA construct into the cell and then maintaining the cell under conditions which allow for formation of the nucleotide integrase. Preferably, the construct is in a vector. Accordingly, the present invention also relates to recombinant vectors comprising a DNA molecule comprising a group II intron. Suitable vectors include, for example, plasmids, phagemid, or viral vector, into which the DNA molecule has been inserted. In the expression vector, the group II intron sequence is operatively linked to an expression control sequence, i.e., a promoter, which directs mRNA synthesis. Representative examples of such promoters, include a retroviral LTR or SV40 promoter, the *E. coli* lac or trp promoters, the phage lambda PL promoter, and other promoters known to control expression of genes in prokaryotic or eukaryotic cells or in viruses. The promoter may also be the natural promoter of the group II intron. The expression vector also contains a ribosome binding site for translation, initiation, and a transcription terminator. Preferably, the recombinant expression vectors also include an origin of replication and a selectable marker, such as for example, the ampicillin-resistance gene of *E. coli*, to permit selection of transformed cells (i.e., cells that are expressing the heterologous group II intron).

Among known viral vectors are recombinant viruses which are generally based on several virus classes including poxviruses, herpesviruses, adenoviruses, parvoviruses and retroviruses. Recombinant viruses of the vaccinia and other types are mentioned and cited, for example, in a review by Mackett, Smith and Moss, *J Virol.* 49:857-864, 1994. Preferably, the virus vector is a defective adenovirus which has the DNA construct inserted into its genome. The term "defective adenovirus" refers to an adenovirus incapable of autonomously replicating in the target cell. Generally, the genome of the defective adenovirus lacks the sequences necessary for the replication of the virus in the infected cell. Such sequences are partially, or preferably, completely removed from the genome. To be able to infect target cells, the defective virus must contain sufficient sequences from the original genome to permit encapsulation of the viral particles during packaging of the construct. Preferably, the adenovirus is of a serotype which is not pathogenic for man. Such serotypes include type 2 and 5 adenoviruses (Ad 2 or Ad 5). In the case of the Ad 5 adenoviruses, the sequences necessary for the replication are the E1A and E1B regions.

More preferably, the virus vector is an immunologically-inert adenovirus. Methods for preparing immunologically-inert adenoviruses are described in Parks et al., *Proc Natl Acad Sci USA* 93:13565-13570, 1996; Leiber, A. et. al., *J. Virol.* 70:8944-8960, 1996; Hardy S., et. al, *J. Virol.* 71:1842-1849, 1997; and Morsy et. al, *Proc. Natl. Acad. Sci. USA* 95:7866-7871, 1998; which are specifically incorporated herein by reference.

Following introduction of the DNA construct into the host cell, the group II intron DNA sequence and the protein-encoding sequences are expressed in the host cell such that excised RNA molecules encoded by the introduced group II intron DNA sequence and protein molecules encoded by the protein-encoding sequence are formed in the cell. The excised group II intron RNA and group II intron-encoded protein are combined within the host cell to produce the nucleotide integrase.

The method used to introduce the DNA molecule is related to the particular host cell used. Suitable host cells are those which are capable of expressing the group II intron DNA sequence. Suitable host cells include, for example, bacterial cells, yeast cells, mammalian cells, and plant cells. In those instances where the host-cell genome and the group II intron DNA sequence use different genetic codes, it is preferred that the DNA construct be modified to comprise codons that correspond to the genetic code of the host cell. The DNA construct, typically, is constructed de novo from synthetic oligonucleotides or modified by in vitro site-directed mutagenesis of an unmodified group II intron DNA or RNA sequence. Optionally, DNA molecules comprising sequences that encode factors that assist in RNA or protein folding, or that inhibit RNA or protein, are also introduced into the cell.

The intron sequence and protein-encoding sequence of the DNA construct are then expressed in the host cell to provide a transformed host cell. As used herein, the term "transformed cell" means a cell which contains RNP particles comprising the excised transcript of the group II intron and the group II intron encoded protein.

The following examples of methods are for illustration only and are not intended to limit the scope of the invention.

EXAMPLES

Example 1

The *E. coli* Genetic Assay

For the L1.LtrB intron, from *Lactococcus lactis*, the preferred DNA target site extends from about position −26 in the 5' exon (E1) to +9 in the 3' exon (E2; positions numbered from the intron-insertion site) (FIG. 1A). In about 14-nucleotide (nt) region of the DNA target site (E1−13 to E2+1) is recognized primarily by base pairing with the intron RNA. This region includes short sequence elements denoted IBS2, IBS1, and δ', which are complementary to intron sequences EBS2, EBS1, and δ (IBS and EBS refer to intron and exon binding sites, respectively) (FIGS. 1A and B). These same sequence elements are involved in base-pairing interactions required for RNA splicing. The regions of the DNA target site flanking the IBS and δ' sequences are recognized by the IEP (intron-encoded protein). The protein first recognizes a small number of nucleotide residues in the distal 5' exon region (E1−26 to −11) and appears to cause local DNA unwinding, enabling the intron to base pair to the IBS and δ' sequences for reverse splicing. Antisense-strand cleavage occurs after reverse splicing and requires additional interactions between the protein and 3' exon.

The genetic assay is based on the ability of a modified L1LtrB intron, from *Lactococcus lactis*, to insert into a target site upstream of a promoterless reporter tene (tetr$^R$), thereby activating the expression of that gene (FIG. 1C). In this assay, a modified L1.LtrB intron, containing a phage T7 promoter near its 3' end is expressed from a T7lac promoter in a chloramphenicol-resistant (Cam$^R$) donor plasmid (pACD-LtrB). A compatible ampicillin-resistant (Amp$^R$) recipient plasmid (pUCR-LtrB/Tet) contains the L1.LtrB target site (ligated E1-E2 sequence) inserted upstream of a promoterless tetracycline-resistance (tet$^R$) gene, so that movement of the intron into the target site activates the expression of that gene. To assay mobility, the donor and recipient plasmids were co-transformed into an *E. Coli* (DE3) strain, which contains an IPTG-inducible T7 RNA polymerase. After induction with 2 mM IPTG, cells co-transformed with the wild-type donor and recipient plasmids gave 10-40% Amp$^R$Tet$^R$ colonies indicative of mobility events, compared to $10^{-5}$ for cells transformed with the Amp$^R$ recipient plasmid alone. Correct integration of the intron was confirmed by DNA sequencing of ten mobility events.

Efficient mobility was abolished by mutations that delete a large segment of the intron open reading frame (ΔORF), inhibit the RT (YAAA) or DNA endonuclease (ΔZn or ΔConZn) activities of the IEP, or inhibit the ribozyme activity of the intron RNA (ΔD5). Further, in experiments using a "twintron" construct, in which a self-splicing group I intron was inserted into the group II intron, 95% of the mobility products had spliced the td intron, confirming that mobility occurs through an RNA intermediate. Deletion analysis showed that a target site extending from position −25 to +9 was sufficient for maximal mobility, whereas further 5' deletions to −13 reduced mobility ~7000-fold, and 3' deletions to +4 reduced mobility ~240-fold.

Figure 10A:
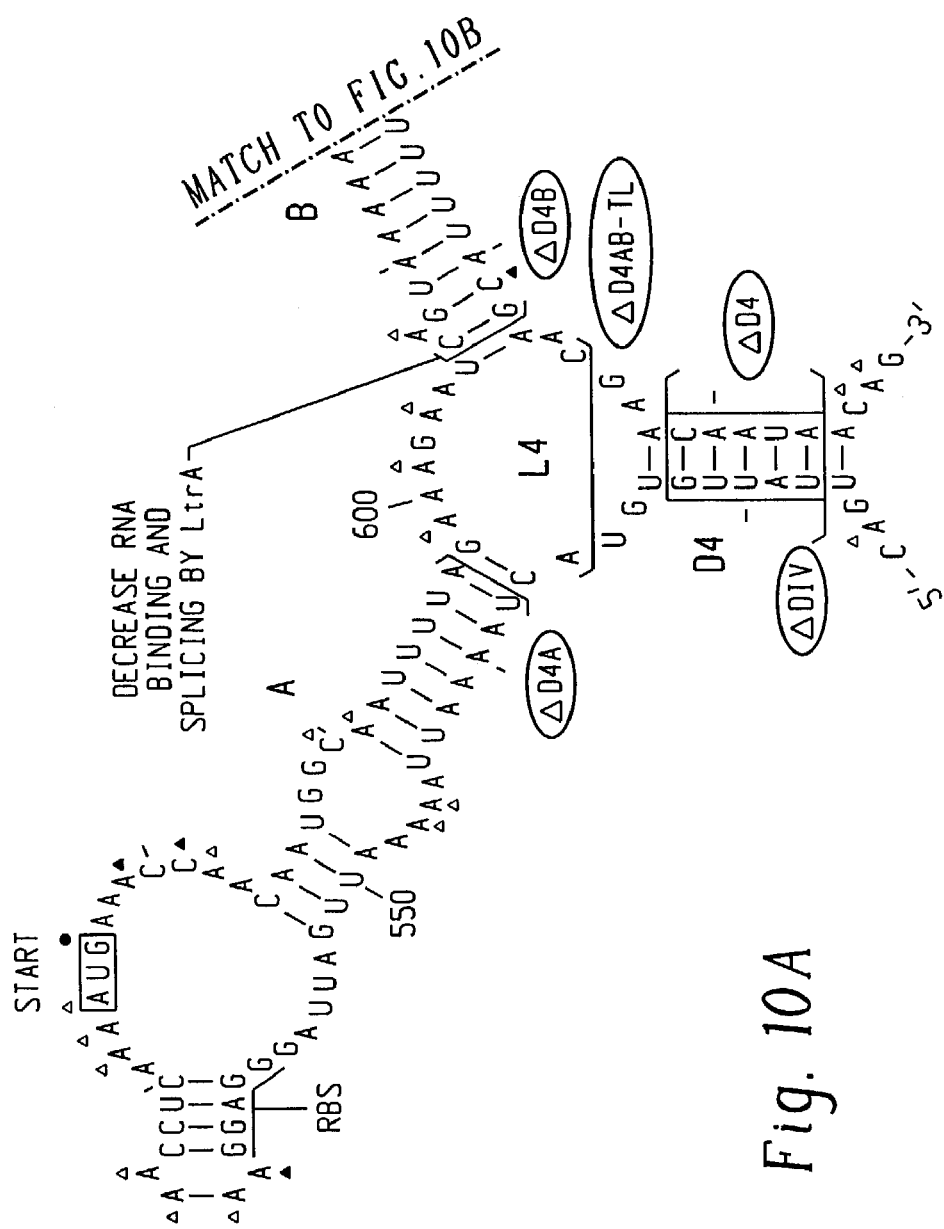
FIG. 10. Representation of the secondary structure of domain IV of the L1.ltrB intron (SEQ ID NO: 39).
Figure 10B:
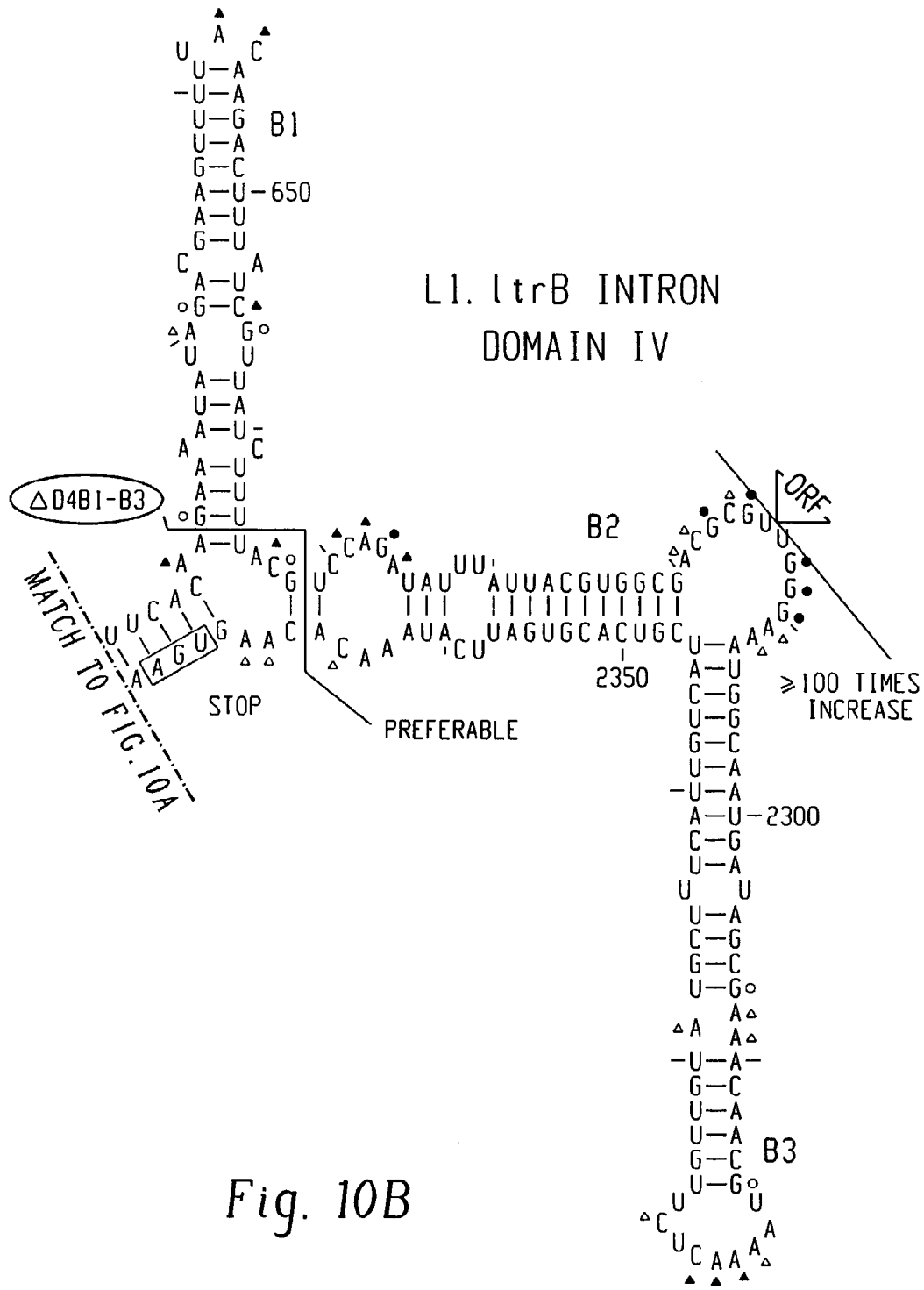

The mobility frequency was increased dramatically by using the donor plasmid pACD-ΔORF+ORF1 (FIG. 1D). This plasmid has a large deletion in the "loop" of intron domain IV (FIG. 10), which removes most of the LtrA ORF, and expresses the LtrA protein separately from a position downstream of the 3' exon. This configuration gave very high mobility frequencies (~70% Tet$^R$ colonies), even without IPTG induction to stimulate donor plasmid transcription, and the frequencies increased to 100% with a low concentration of IPTG (100 μM). The increased mobility frequencies appear to be due to greater resistance of the ΔORF intron to nucleolytic cleavage in domain IV rather than increased expression of the LtrA protein.

Example 2

Identification of Preferred Nucleotides in the L1.LtrB DNA Target Recognition Site The very high mobility frequencies enabled a test of detailed target-site recognition rules for the wild-type L1.LtrB intron by performing mobility assays, as described in Example 1, with recipient plasmids in which positions −30 to +15 of the L1.LtrB target site were partially randomized (30% "doped" with non-wild-type nucleotide residues). Methods. To construct the recipient plasmid library, a 79-nt synthetic oligonucleotide 5' GCGGCGACGTC ACCCACGTCGATCGTGAACACATCCAT AACCATATCATTTTTAATGAATTCGATACCGTCGAC-CTCGA, (SEQ ID NO: 1), which contains the doped region (underlined), was made double-stranded by using Taq DNA polymerase with a primer 5'-TCGAGGTCGACGGTATC (SEQ ID NO: 2, complementary to its 3' end. The double-stranded DNA was then digested with Aat II and Eco RI and cloned between the corresponding sites of the polylinker of pBRR-Tet (13). The library was electroporated into *E. coli* DH10B and amplified in LB medium. The diversity of the initial pool was ~4×10$^6$. Mobility assays were carried out with the wild-type pACD-ΔORF+ORF2 donor plasmid, except that cells were transformed by electroporation, IPTG induction was omitted, and the tetracycline concentration was increased to 50 μg/ml to decrease the background of partially tetracycline-resistant colonies resulting from cryptic, weak promoters introduced with the doped target sequences. ~3.1× 10$^6$ Amp$^R$Cam$^R$ cotransformants were obtained, of which 3% were Tet$^R$. By comparison, ~2% of the colonies with recipient plasmids alone were also Amp$^R$Tet$^R$, indicating that only ~1% of cotransformants were real mobility events, with the remainder presumably resulting from promoters generated by random sequences in the pool of DNA target sites. Sequences were determined for 111 mobility products and 104 plasmids from the original recipient plasmid pool (FIGS. 2A and B).

Figure 2A:
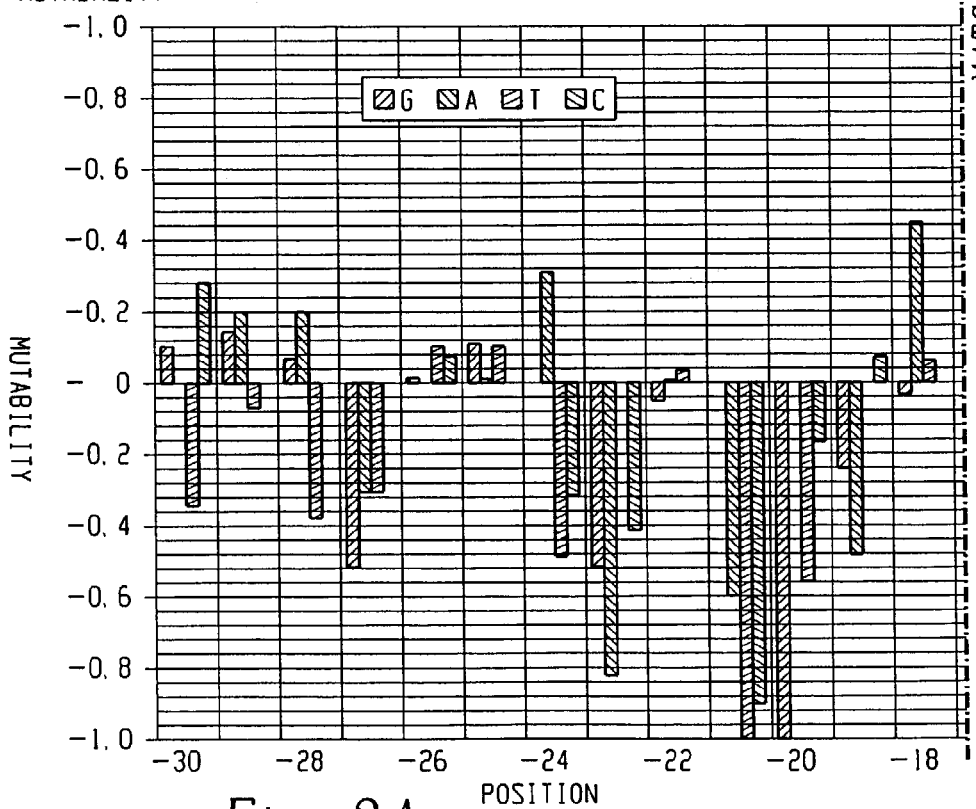
FIG. 2. Nucleotide frequencies in active DNA target sites. A mobility assay was performed with the wild-type donor plasmid pACD-ΔORF+ORF2 (17) and a recipient plasmid pool in which DNA target sites positions between −30 and +15 were partially randomized ("doped") to contain 70% of the wild-type nucleotide and 10% of each of the three mutant nucleotides. (A) shows nucleotide frequencies in active DNA target sites ("selected"), based on sequencing 111 mobility products using outward pointing primers near the intron's 5' and 3' ends, and (B) shows nucleotide frequencies in the original recipient pool, based on sequencing 104 randomly chosen plasmids using a primer downstream of the target site. The wild-type nucleotide residue at each position is highlighted by a thick box. (C) shows mutability values at each position of the DNA target site. The mutability values were calculated by comparing the ratios (R) of mutant to wild-type nucleotide residues at each position in the active target sites and the original recipient plasmid pool by using the expression $[(R_{mut/wt})_{selected}/(R_{mut/wt})_{pool}]-1$ (23)(SEQ ID NOS 12 & 14 are disclosed respectively in order of appearance).

To assess which positions are potentially recognized by base pairing (i.e., the IBS/δ' region of the target recognition site is potentially recognized by base pairing with the intron RNA), the number of potential base pairs at each position between −13 and +4 in the selected target sites was compared with those in the original recipient plasmid pool (FIGS. 2A and B). Comparison of the number of potential base pairs in selected target sites and the original recipient pool showed some selection for base pairing at each position between −13 and +4, except for −7, which instead showed clear selection against base pairing (FIG. 3A). FIG. 3B compares the total number of potential base pairs at these 16 positions in the selected clones with that in the initial pool. The plot shows strong selection for base pairing over these 16 nucleotides, with 99% of the clones selected having 13 potential base pairs compared to 73% of the initial pool. None has less than 12 potential base pairs.

Figure 2B:
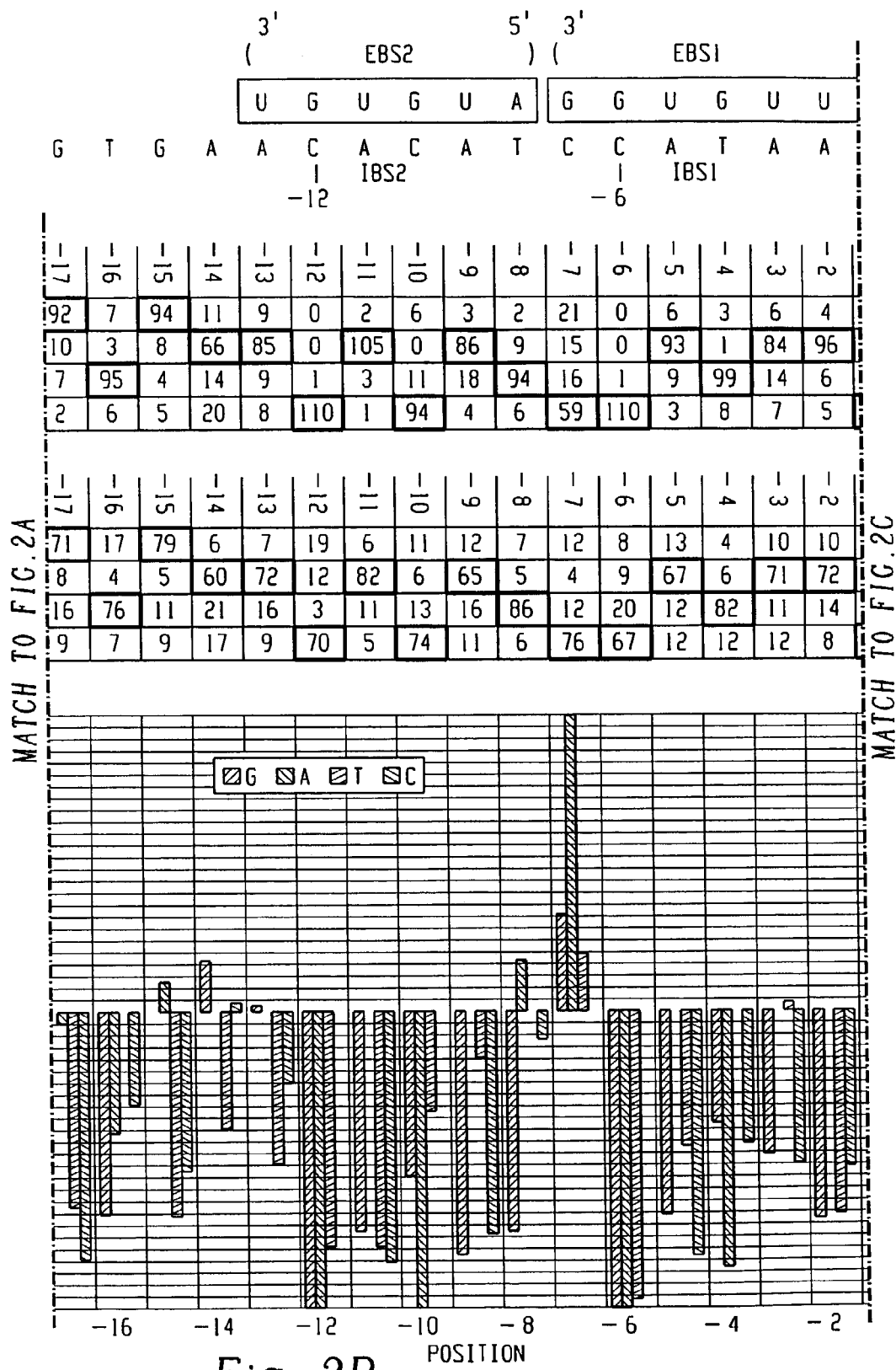
Figure 2C:
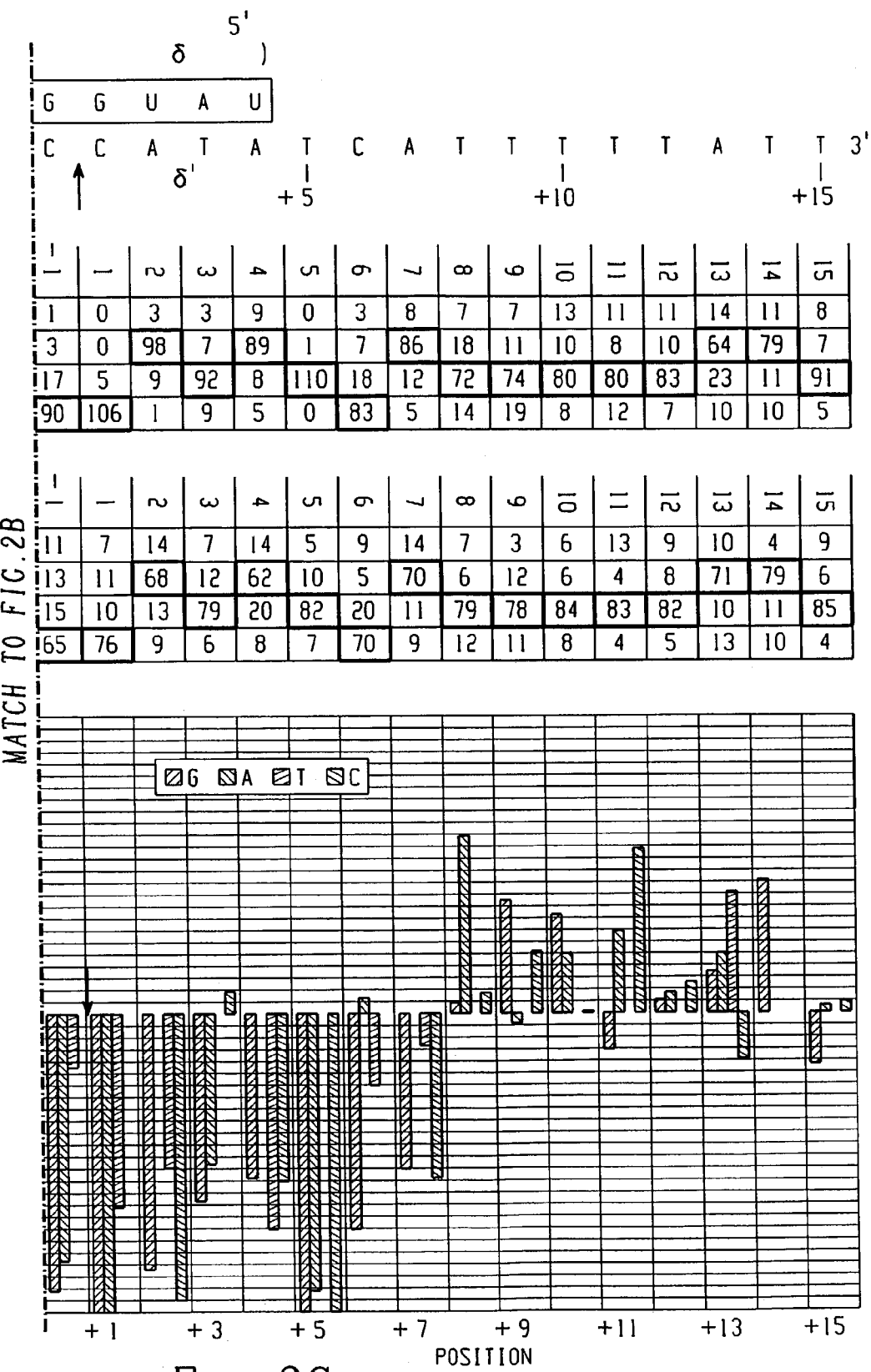
Figure 4A:
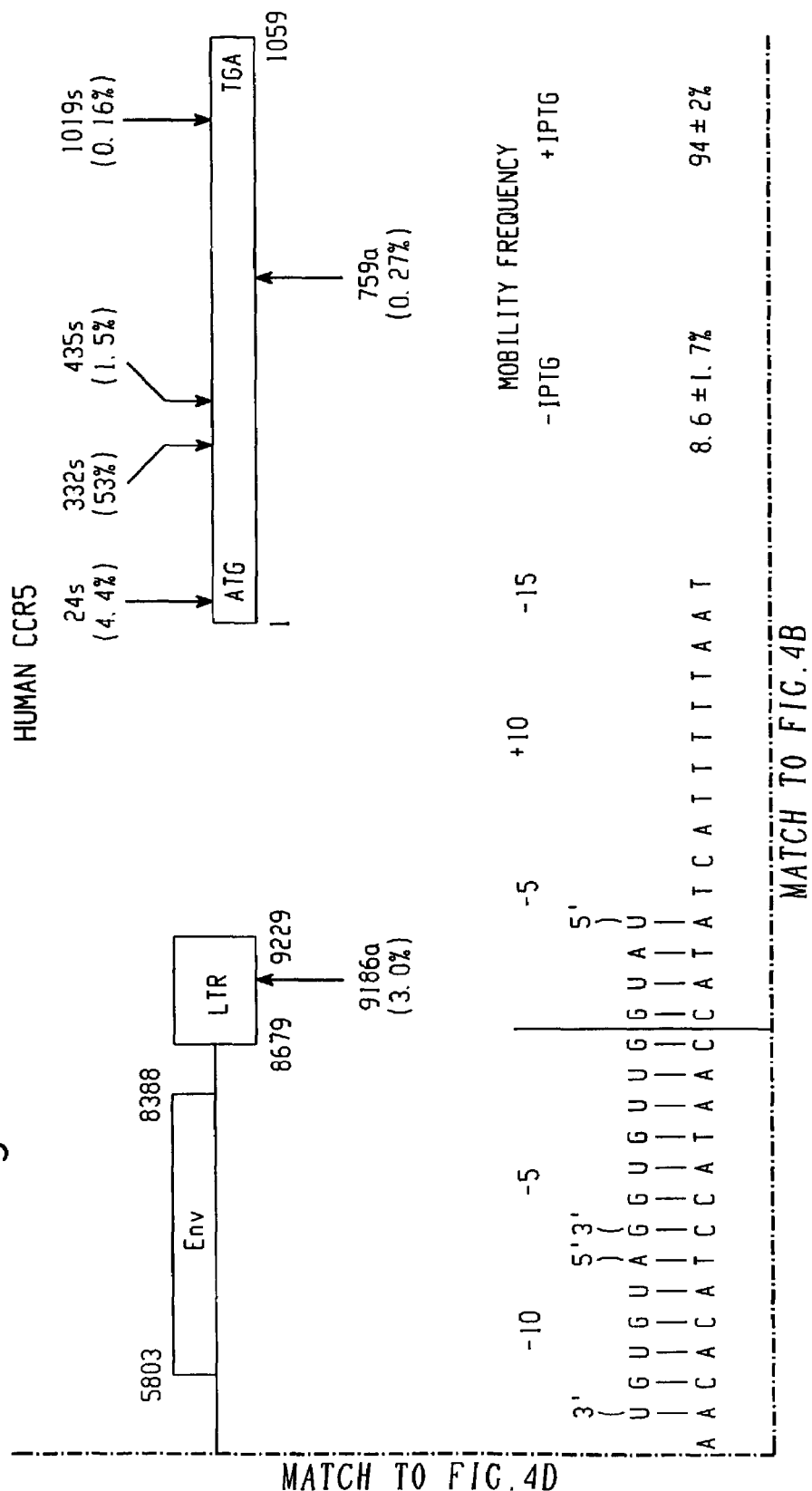
FIG. 4. Design and selection of group II introns that insert into specific DNA target sites. (A) Maps showing group II intron insertion sites in the HIV-1 provirus and human CCR5 gene. Insertion sites in the top (sense) and bottom (antisense) strands are indicated by arrows above and below the target DNA, respectively. Introns are identified by the position number in the target site (HIV-1 sequence, GenBank K02013; CCR5 sequence, GenBank AF031237), followed by "s" or "a" indicating the sense or antisense strand, respectively. The numbers in parentheses indicate mobility frequencies in the *E. coli* genetic assay in the presence of 100 μM IPTG. The intron HIV1-54/9186a has integration sites in each long terminal repeat (LTR). (B) DNA target-site sequences and base-pairing interactions for designed and selected introns. The wild-type L1.LtrB target site and base-pairing interactions are shown above for comparison. Nucleotide residues in the HIV-1 and CCR5 target sites that match the wild-type sequence are boxed. Mobility frequencies in the presence or absence of 100 μM IPTG (mean+/−S.D. for at least two experiments) are shown to the right. Mobility events were confirmed by sequencing a region extending from a position downstream of the intron's EBS sequences through the 5' junction with the target DNA, using primer LtrBA2 (complementary to intron positions 301-326). To determine mobility frequencies, the selected introns were reconstructed in the donor plasmid via PCR, and tested in the *E. coli* genetic assay with the indicated recipient plasmids containing the HIV-1 or CCR5 target sites. The selected introns HIV1-54a/9186a and 2654a have mismatches in the EBS-IBS and δ-δ' interactions, and their mobility frequencies increased substantially when these were "corrected". (SEQ ID NOS 12-13 & 15-38 are disclosed respectively in order of appearance).
Figure 4C:
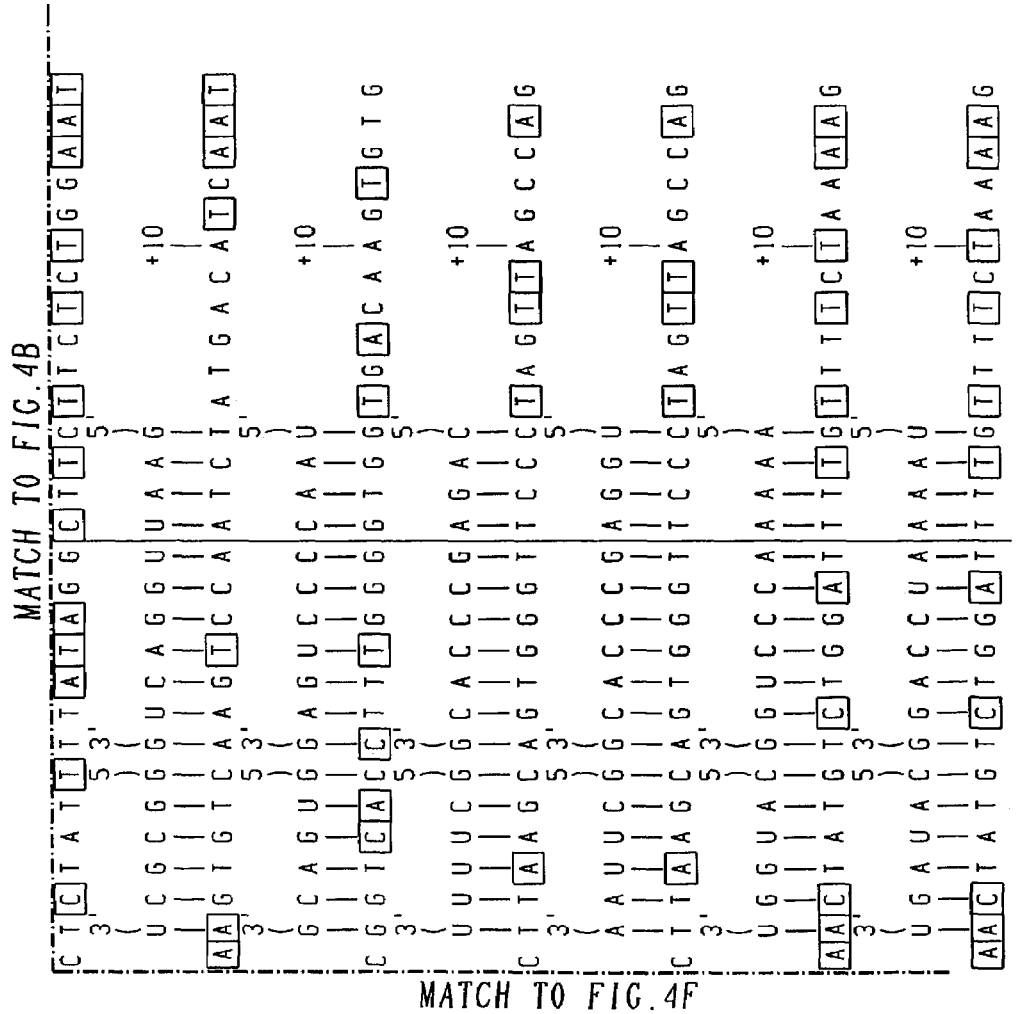
Figure 4D:
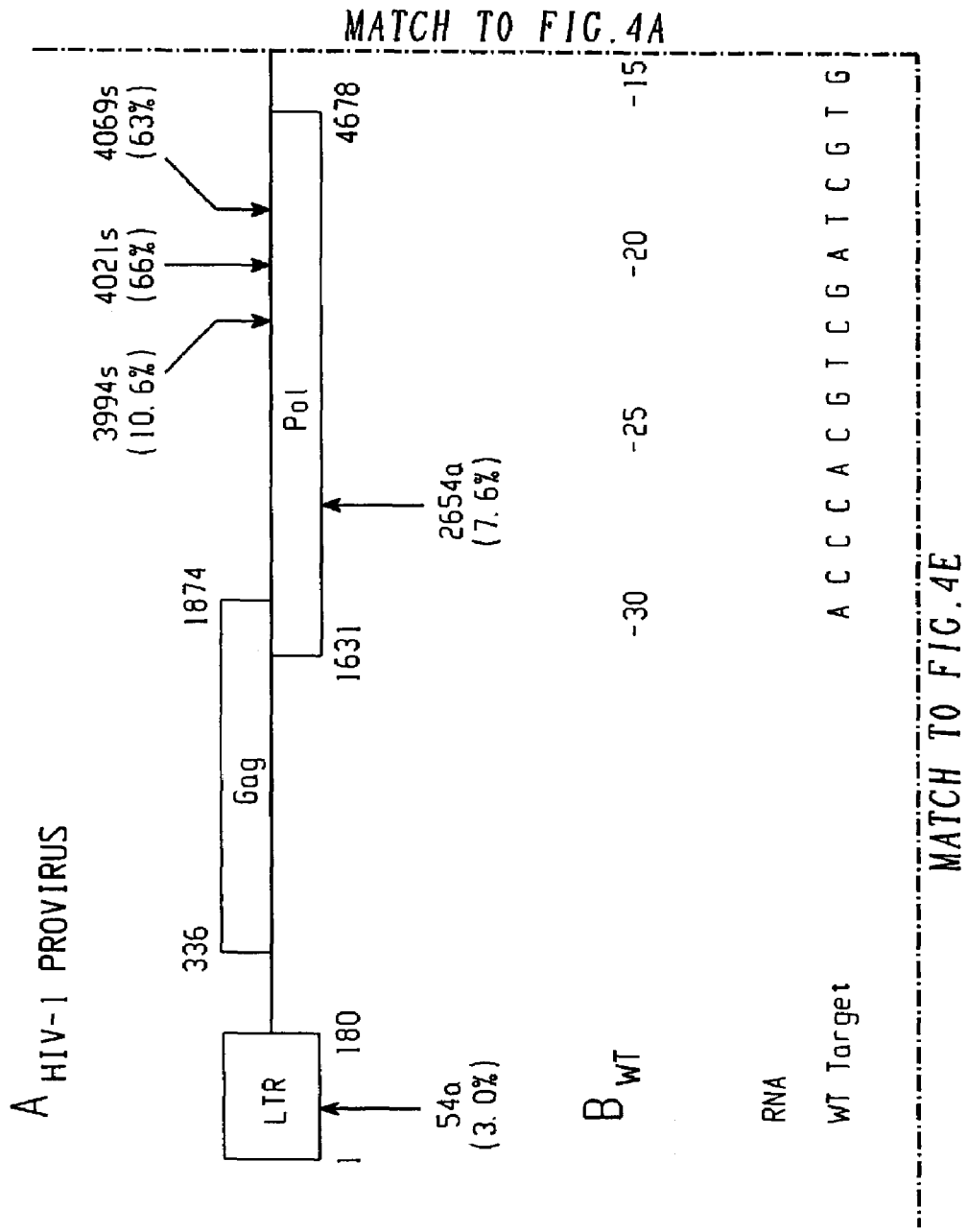
Figure 4E:
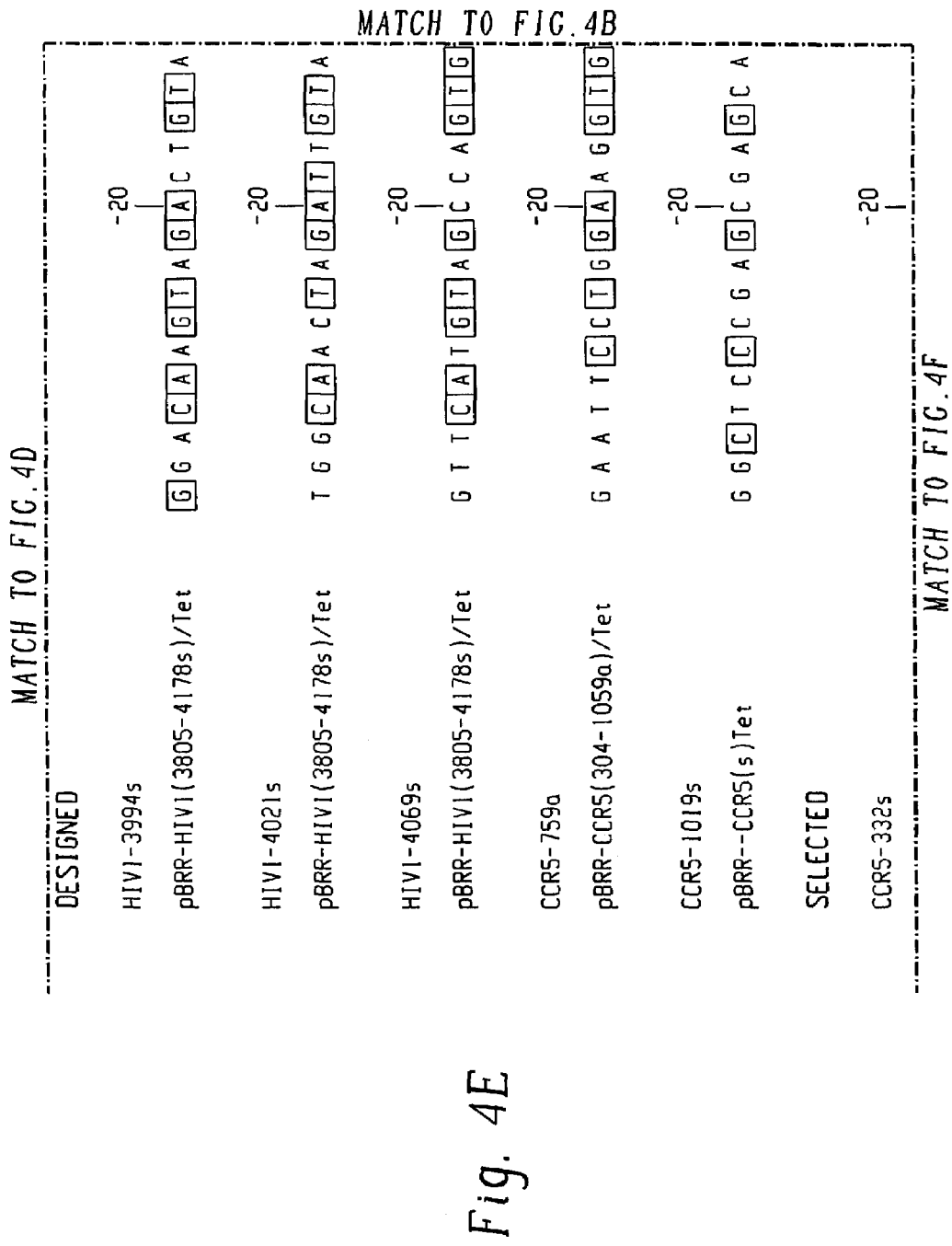

The effect of nucleotide substitutions at each position was analyzed by comparing the ratios (R) of mutant to wild-type nucleotide residues in active DNA target sites with those in the initial recipient pool by using the expression $[(R_{mut/wt})_{active}/(R_{mut/wt})_{pool}]-1$. The resulting "mutability values" are plotted in FIG. 2C. A negative value indicates selection against the substituted nucleotide residue, with a maximum negative value of −1 indicating that the nucleotide is totally absent in active DNA target sites. A value of 0 indicates a neutral substitution, and a positive value indicates that the substituted nucleotide is preferred over the wild-type nucleotide. To normalize to the same scale, the maximum positive value in the experiment, 3.83 for the substitution C-7A, was set equal to +1.

The data show that most of the wild-type nucleotide residues between positions −24 and +7 were selected to some extent. In the protein-recognition regions, the most critical positions were readily identified as G−21 and T+5 (mutability values −0.9 to −1 for most nucleotide substitutions). The present results provide information about every possible nucleotide substitution at each position. For example, the data show that there is significantly less penalty for substitution of an A residue at G−21 than for substitution of a pyrimidine residue (mutability values: A=−0.6, T=−1, and C=−0.9), and that G is strongly selected against at position −20 (mutability value −1), possibly reflecting proximity to the required G at position −21. Moderate selection for the wild-type nucleotide residue was observed at positions −23, −20, −17, −16, −15, +2, +3, +4 and +6 (mutability values $\leq$−0.6 for some substitutions), while selection for mutant nucleotide residues was found from positions +8 to +15 encompassing the antisense-strand cleavage site (positive mutability values).

In the IBS/δ' region of the DNA target site, which is potentially recognized by base pairing with the intron RNA, the data show strong or moderate selection against nucleotide substitutions at positions −13 to −8 of IBS2, positions −6 to −1 in IBS1, and positions +1 to +4 in δ'. The most strongly selected positions were −12, −11, −6, and +1 (mutability values $\leq$−0.6 for any substitution), while position −7 showed selection for nucleotides that do not form Watson-Crick base pairs with the intron. Within the region recognized by base pairing, pyrimidine-pyrimidine mismatches are tolerated at some positions, while purine-purine mismatches are selected against at most positions. Positions that correspond to a G-residue in the intron RNA (−12, −10, −6, −4, −1 and +1) showed different degrees of selection against purine-purine mismatches. Positions −1 and +1 showed strong bias against either GG or AG pairs, while positions −10 and −4 showed more bias against GA than GG pairs. These differences may reflect that the purine-purine mismatches have different effects on helix geometry depending on sequence context, or that the mismatches are positioned differently relative to the intron's active site. Positions that correspond to a U-residue in the intron RNA tolerate pyrimidine-pyrimidine mismatches to various degrees, with T more readily substituted than C at several positions (e.g., −9, −5, −3, and +2). Positions −8 and +3, which correspond to A-residues in the intron RNA, did not show strong bias against substitution of a C-residue for the wild-type T-residue in the DNA target site, possibly reflecting that an AC base pair only minimally disrupts an otherwise substantially base-paired helix.

Notably, a number of positions in the IBS/δ' region showed selection for the wild-type nucleotide over other potential base-pairing partners, with particularly strong selection for the wild-type nucleotide evident at positions −12, −11, −6, and +1. The most strongly selected positions, −12 and −6, correspond to a G-residue in the intron RNA that base pairs with a C-residue in the DNA target site. In both cases, the target site C-residue was selected in 110 of 111 target sites, with the single exception corresponding to a T-residue that can also base pair with the intron. The very strong selection for the wild-type nucleotides at C−12 and C−6 could reflect that these positions are recognized in part by the IEP on the strand opposite that which base pairs with the intron RNA. A similar explanation may account for the selection of the wild-type A residue at position −11. Alternatively, the wild-type GC pairs at −12 and −6 may be required to anchor the ends of the duplexes.

Example 3

Design and Selection of Introns that Specifically Integrate into Specific DNA Target Sites Group II introns were designed that targeted to different regions of HIV-1$_{LAI}$ provirus and the human gene encoding the CCR5 chemokine receptor. The latter is required, together with CD4, for infection of macrophages by HIV-1, and it is known that individuals homozygous for CCR5 mutations are resistant to HIV-1 infection. Consequently, disabling CCR5 has been considered a means to block HIV-1 infection and AIDS progression.

For targeting, the HIV-1$_{LAI}$ and CCR5 DNA sequences were scanned for the best matches to the fixed positions recognized by the IEP, and the intron RNA was then modified to base pair to the adjacent sequences for the EBS-IBS and δ-δ' interactions (positions −11 to −8 and −6 to +3 or +4). The data from the initial selection study with partially randomized DNA target sites (FIG. 2) was used to obtain a quantitative measure (i.e., mutability value) of the ability to substitute a nucleotide residue at a particular position. To select target sites in the HIV-1$_{LAI}$ and CCR5 DNAs, a mutability value of −0.6 was initially used as a lower limit for nucleotide substitutions at positions recognized by the IEP (taken as −30 to −12 and +4 to +7 in initial experiments). The resulting search sequence 5' N$_7$(G,T,C)N(G,A)(A,T,C)N$_2$(G,A)(A,T,C)(G,A,C)N$_2$CN$_{11}$↓N$_3$(G,A,C)T(A,T,C)N, where N represents any of the four bases, gave eighteen matches in HIV-1$_{LAI}$ and two in CCR5. The HIV-1 target sites were ordered by successively higher cutoff values, and introns targeted to the two best sites, along with the two CCR5 sites were tested for their ability to insert into HIV-1$_{LAI}$ and CCR5 DNA targets in the E. coli genetic assay (FIG. 1). Also tested was HIV1-4069s, in which position −12 did not meet the −0.6 cutoff, to determine whether the GC base pair at this position, could be replaced with a compensatory AT base pair. Because the retargeted introns have modified EBS and δ sequences, complementary IBS and +1 sequences were introduced into the donor plasmid to ensure efficient splicing.

All of the retargeted introns inserted at precisely the correct positions in the HIV-1 and CCR5 target sites, as confirmed by sequencing multiple events. Two introns, HIV1-4021s and HIV1-4069s, inserted at high frequencies (>60% after IPTG induction), while the remaining three introns (CCR5-1019s, CCR5-759a, and HIV1-3994s) inserted at lower frequencies (0.16 to 10.6%). The two most efficient introns have compensatory changes at EBS-IBS and δ-δ' positions −12, −6 or +1, where the wild-type nucleotide was strongly conserved in the initial selection, indicating that protein recognition at these positions is not essential for efficient integration. The less efficient introns presumably have deleterious combinations of nucleotides that are not readily predicted at this stage.

To alleviate the necessity of predicting such deleterious combinations, an alternate, selection-based approach was developed in which the desired DNA target site is simply cloned in the recipient vector upstream of the promoterless $tet^R$ gene, and introns that insert into that site are selected from a combinatorial library having randomized target-site recognition sequences (EBS and δ). To eliminate selection for the wild-type EBS sequences during RNA splicing in vivo, the corresponding IBS sequences in the 5' exon of the donor plasmid library were also randomized. Although the requirement for base pairing between the two sets of randomized sequences in unspliced precursor RNA reduces the complexity of the spliced intron pool, the approach was successful because of the very high integration efficiency in this system.

Single transformations with the combinatorial library yielded thirteen introns that inserted at different positions in the HIV-$1_{LA1}$ and CCR5 target sites. The introns were retested individually and shown to integrate into their target sites at frequencies ranging from <$10^{-5}$ to 53%. Data for a subset of the selected introns are summarized in FIG. 4. Most of the efficient introns selected target sites having the G−21 and T+5 residues, which were found to be critically required for protein recognition. However, introns HIV1-54a/9186a and CCR5-24s deviate at these positions, but still insert at frequencies of 3-5%, possibly reflecting partial compensation by other target-site nucleotide residues.

The most efficient CCR5 target site has a disfavored nucleotide residue at position −16, which excluded it from the initial computer search for potential target sites. Two of the selected HIV-1 introns have mismatches in EBS-IBS and δ-δ' interactions, and their integration efficiencies increased substantially when these were "corrected". Such correction can be effected routinely via appropriate PCR primers in the process of recloning the selected intron into the donor plasmid. Although the selected introns have a range of mobility frequencies, it should be relatively straightforward to enrich for the most efficient introns by carrying out multiple rounds of selection.

Example 4

Function of Modified Introns in Mammalian Cells

Figure 5:
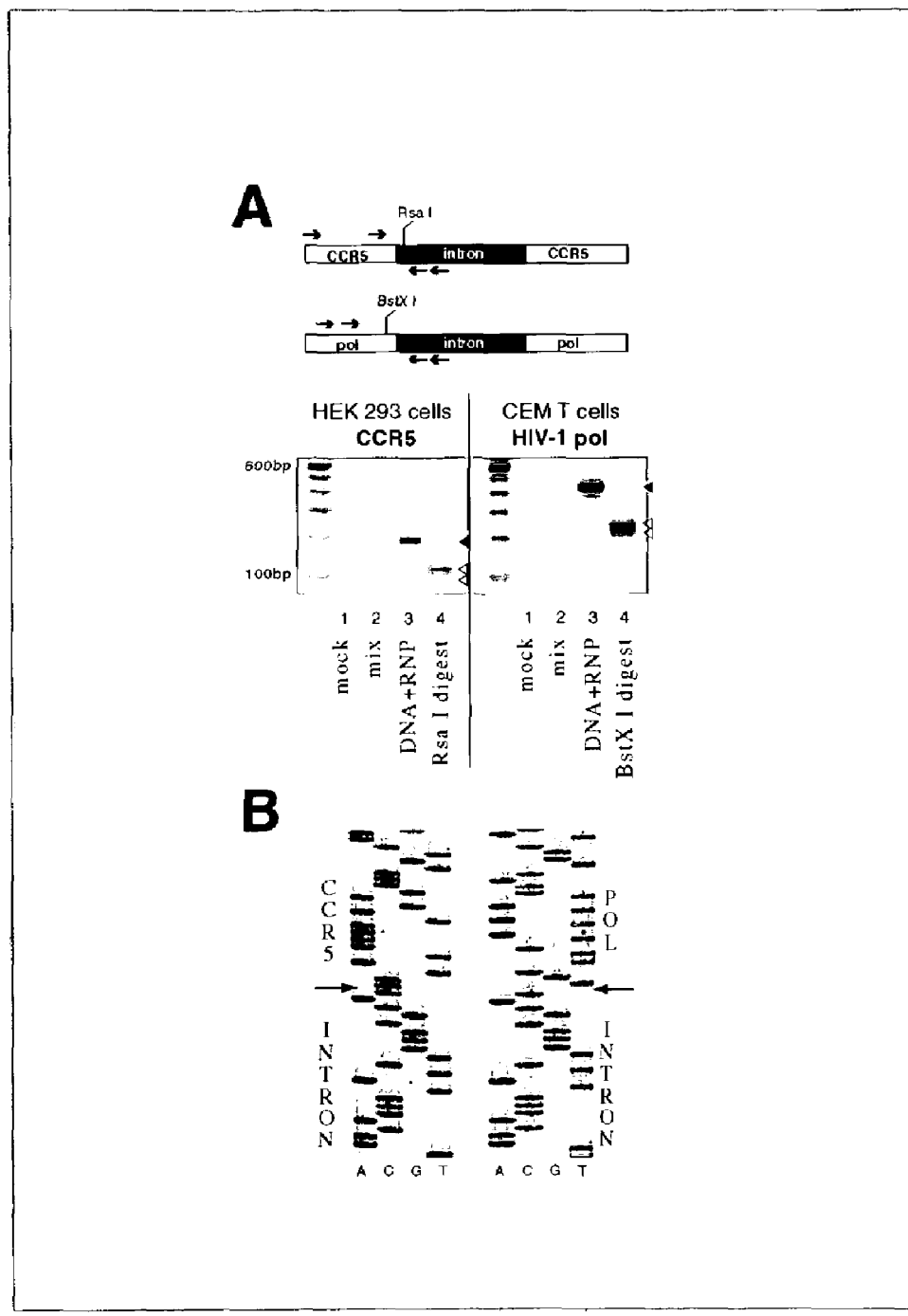
FIGS. 5A and B. Intron insertion into CCR5 and HIV-1 pol genes in human cell lines. (A) PCR amplification of integration junctions. Integration events into the CCR5 and HIV-1 pol genes are shown schematically at the top. Primer sites are designated by arrows, and restriction sites are labeled. PCR products were analyzed in a 2% agarose gel. Closed arrowheads indicate PCR products corresponding to 5' integration junctions in the CCR5 (left) and HIV-1 pol (right) genes. Open arrowheads indicate the restriction fragments of integration products. The left lane shows molecular weight markers. (B) Representative sequencing gels for intron integration into the CCR5 (left) and HIV-1 pol (right) genes. The arrows denote integration junctions.

To determine if group II intron RNPs can function in a human cellular environment, 293 embryonic kidney cells or CEM T-cells were cotransfected with plasmids containing either CCR5 or HIV-1 DNA targets and RNP particles containing the retargeted introns (CCR5-332s or HIV1-4069s), which had been packaged separately into liposomes. PCR analysis of DNA isolated from the transfected cells gave products expected for integration of the introns into the DNA target sites (FIG. 5A). By contrast, such products were not detected with DNA from mock-transfected cells, from the transfection mix incubated without cells, nor from cells that were transfected separately with either target DNA or RNPs and mixed prior to DNA extraction. Restriction enzyme analysis and sequencing confirmed that the retargeted introns had inserted at the correct locations in the CCR5 and HIV-1 DNAs (FIGS. 5A and B).

Example 5

Construction of Combinatorial Donor Plasmid Libraries

As described in Example 3, a selection-based approach was developed in which the desired DNA target site is simply cloned into the recipient vector upstream of the promoterless $tet^R$ gene, and introns that insert into that site are selected from a combinatorial donor library having randomized target-site recognition sequences (EBS and δ). The descriptions in this example demonstrate how the donor libraries were made. These donor libraries were used in the assay described in Example 1.

Two donor libraries were made. In the first donor library, pACD-ΔORF+ORF2 library 1, hereinafter designated as "library 1", intron positions that could potentially base pair with target site positions −13 to −8 (IBS2) and −6 to +4 (IBS1+δ' region) were randomized, along with positions −1 to −13 of the 5' exon. In the second donor library, pACD-ΔORF+ORF2 library 2, hereinafter designated as "library 2", intron positions that could potentially base pair with target site positions −12 to −8 (IBS2) and −6 to +3 (IBS1+δ' region) were randomized, along with positions −1 to −12 of the 5' exon. Library 2 was made because there were additional results indicating that the preferred base pairing sequences for IBS2-EBS2, IBS1-EBS1 and □-□' extend from −12 to −8, −6 to −1 and +1 to +3, respectively.

Description of how both donor libraries were made follow below.

Figure 8:
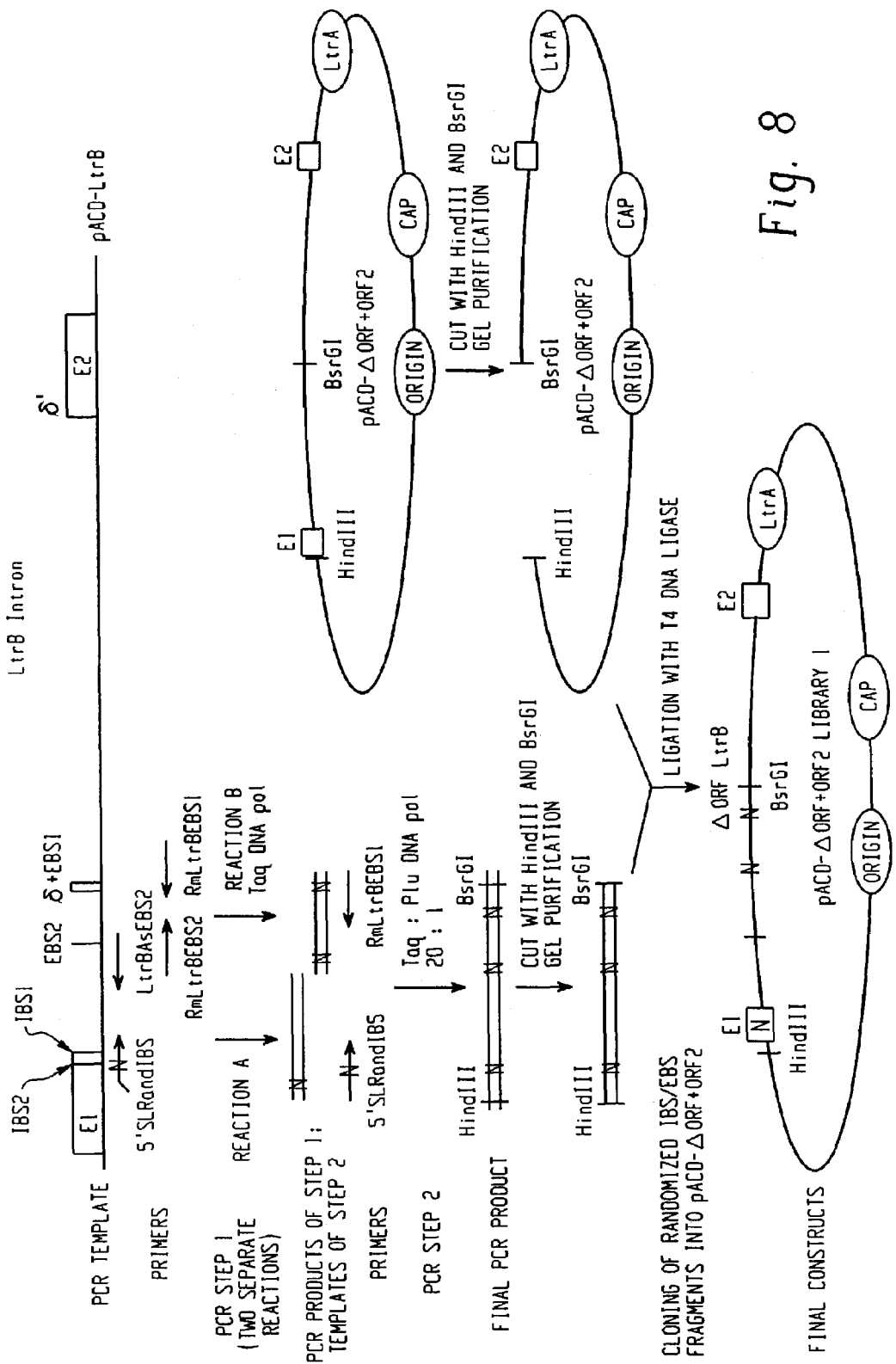
FIG. 8. Schematic representation of the method used to prepare pACD-ΔORF+ORF2 library 1.

Library 1 was constructed as shown in FIG. 8. The randomized sequences were introduced via primers in a two-step PCR procedure. In the first step pACD-LtrB, which contains the full-length L1.LtrB intron, flanked by 177 nts of exon 1 and 90 nts of exon 2, was used as a template. A first set of primer pairs, 5' SLR and IBS and LtrBAsEBS2 were used to generate a first group of PCR products which extends from position −26 in E1 through position 222 in the intron, and a second primer pair, RmLtrBEBS1 and RmLTRBEBS2 was used to generate a second PCR product which extends from position 202 to 318 in the intron. The two partially overlapping PCR products produced in this first PCR step were gel purified and then mixed and PCR-amplified using Taq and Pfu DNA polymerases (mixed in a 20:1 ratio in units) with the primers 5'SLR and IBS and RmLtrBEBS1, which also contains HindIII site and BsrGI site, respectively. The primers used in the second PCR step are complementary to position −26 in the 5' exon to position 18 in the intron and position 259 to position 318 in the intron. The final PCR products were then digested with restriction enzymes HindIII and BsrGI and ligated between the corresponding sites of pACD-DORF+ORF2 plasmid. The ligation products were then electroporated into *E. coli* DH10B cells (obtained from Life Technologies). The electroporated cells were grown in bacterial growth media at 37° C. for 1 hour for rescue and small aliquots of cells were plated on LB+Cap plates to estimate the number of independent transformants. The library was amplified in LB medium containing chloramphenicol. Assuming that most or all of the independent transformants would be different from each other, the diversity of the library was estimated to be the number of total independent transformants. However, in this case the diversity would theoretically be twice the number of the total independent transformants because the IBS and EBS1 region were randomized and unpaired in most of the fragments cloned in the pACD-DORF+ORF due to randomization of IBS and EBS1 regions in the two oligos used in the final PCR step. Therefore, each plasmid transformed would make two different plasmids after replication. The diversity of the library was estimated to be $2.0 \times 10^8$.

Oligos used in library construction are:

5'SLR and IBS:

5'-AAA AAA GCT TCG TCG ATC GTG ANN NNN NNN NNN NNN NNG TGC GCC CAG ATA GGG TG-3' (SEQ ID NO: 3)

LtrBAsEBS2:

5'-AAC CGA AAT TAG AAA CTT GCG TTC AG-3' (SEQ ID NO: 4)

RmLtrBEBS1:

5'-CAG ATT GTA CAA ATG TGG TGA TAA CAG ATA AGT CNN NNN NNN NNA CTT ACC TTT CTT TGT-3' (SEQ ID NO: 5)

RmLtrBEBS2:

5'-CGC AAG TTT CTA ATT TCG GTT NNN NNN CGA TAG AGG AAA GTG TCT-3' (SEQ ID NO: 6).

The "N" in each oligo indicates each randomized position.

Figure 9:
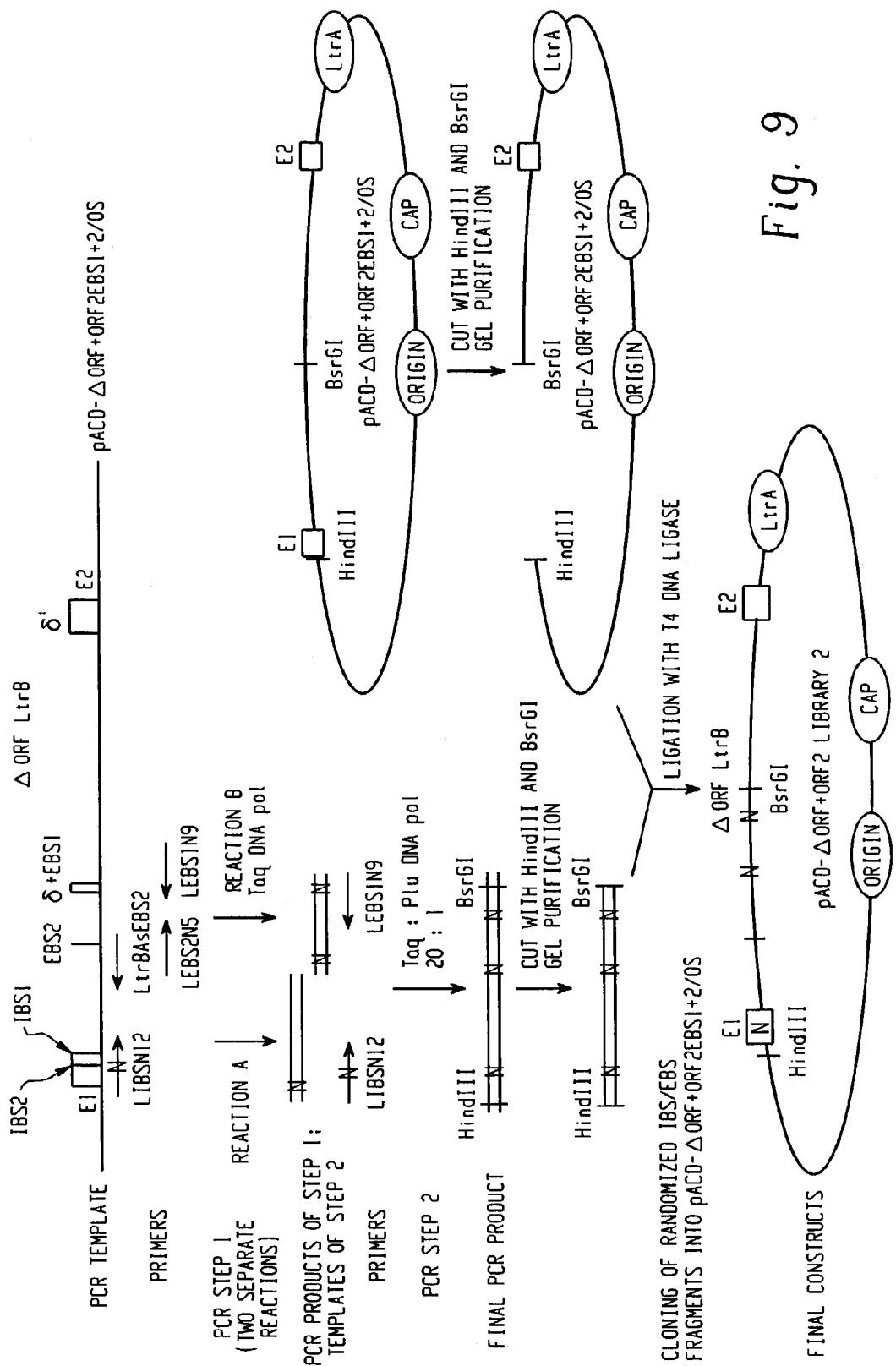
FIG. 9. Schematic representation of the method used to prepare pACD-ΔORF+ORF2 library 2.

Library 2 was constructed as shown in FIG. 9. In general, the steps are the same as described above for library 1. DNA fragments containing the randomized regions were generated using two-step PCR. In the first step, two partially overlapping PCR fragments were generated from plasmid pACD-ΔORF+ORF2EBS1+2/OS using Taq DNA polymerase with primer pair LIBSN12 and LtrBAsEBS2 and another primer pair LEBS1N9 and LEBS2N5. The plasmid pACD-ΔORF+ORF2EBS 1+2/OS is a nonfunctional derivative of pACD-ΔORF+ORF2 because the intron is not spliceable with each nucleotide residue that potentially base pairs with target site positions –7 to +4 (EBS1 and δ region) and –13 to –8 (EBS2 region) switched to its complementary nucleotide residue. The randomized sequences in IBS, EBS1 and S, and EBS2 were introduced into the primers LIBSN12, LEBS1N9 and LEBS2N5 during the oligonucleotide synthesis. Each PCR reaction was carried out in 100 μl reaction medium containing 20 mM Tris-HCl (pH 8.4), 50 mM KCl, 2.5 mM $MgCl_2$, 0.2 mM each of dATP, dCTP, dGTP and dTTP, 0.1 units/μl Taq DNA polymerase (Life Technologies, Gaithersburg, Md.), 10 ng of template pACD-ΔORF+ORF2EBS1+2/OS and 800 ng each of primers LIBSN12 and LtrBAsEBS2 for reaction A and 800 ng primer LEBS2N5 and 1.2 μg primer LEBS1N9 for reaction B. Ten reactions each of reaction A and B were carried out by first being denatured at 94° C. for 2 minutes, then followed with 30×(94° C., 1 minute; 60° C. 30 seconds; 72° C., 2 minutes) and then 72° C. for 10 minutes. The PCR products were then extracted with phenol:chloroform:isoamyl alcohol (Phenol-CIA; 25:24:1) and precipitated with ethanol. The PCR products were then purified on 1% agarose gel. In the second step, the two partially overlapping PCR products were mixed and PCR-amplified using Taq and Pfu DNA polymerases (mixed in a 20:1 ratio in units) with the primers LIBSN12 and LEBS1N9, which also conain HindIII site and BsrGI site, respectively. 5 PCR reactions were carried out with each in 100 μl reaction medium containing 20 mM Tris-HCl (pH 8.4), 50 mM KCl, 5.0 mM $MgCl_2$, 0.2 mM each of dATP, dCTP, dGTP and dTTP, 0.1 units/μl Taq DNA polymerase (Life Technologies) and 0.005 units/μl Pfu DNA polymerase (Strategene, La Jolla, Calif.), 800 ng each of primers LIBSN12 and LEBS1N9, and about 4 μg of the IBS containing fragment and 2 μg of the EBS1EBS2 containing fragment. The reactions were carried out by first being denatured at 94° C. for 2 minutes, then followed with 25×(94° C., 1 minute; 60° C. 30 seconds; 72° C., 2 minutes) and then 72° C. for 10 minutes. The final PCR products were then phenol-CIA extracted and ethanol precipitated as in the first step.

To clone the PCR amplified fragments into pACD-ΔORF+ORF2EBS1+2/OS, half of the final PCR products were digested with restriction enzymes HindIII and BsrGI in a 200 μl reaction medium containing 50 mM NaCl, 10 mM Tris-HCl, 10 mM MgCl2, 1 mM dithiothreitol (DTT) (pH 7.9@25° C.), 1 μg/ml bovine serium albumim (BSA), 300 units HindIII (New England Biolab, Beverly, Mass.) and 150 units BsrGI (New England Biolab) at 37° C. for 6 hours 30 minutes. For the vector, 90 μg of the pACD-ΔORF+ORF2EBS1+2/OS plasmid was also digested with HindIII and BsrGI in a 250 μl reaction medium containing 50 mM NaCl, 10 mM Tris-HCl, 10 mM $MgCl_2$, 1 mM dithiothreitol (DTT) (pH 7.9@25° C.), 1 μg/ml BSA, 300 units HindIII (New England Biolab) and 150 units BsrGI (New England Biolab) and 5 units alkaline phosphotase (Boehringer Mannheim, Indianapolis, Ind.) at 37° C. for overnight. The digestion products were gel purified using 1% agarose gel. The HindIII and BsrGI digested 339-nt PCR fragment and 5987-nt vector were ligated in a 500 μl reaction medium containing 50 mM Tris-HCl (pH 7.5), 10 mM $MgCl_2$, 10 mM dithiothreitol, 1 mM ATP, 25 μg/ml BSA, 40 units/μl T4 DNA ligase (New England Biolab) and 5 μg the HindIII/BsrGI digested 339-nt RandIBSEBS fragment and 10 μg HindIII/BsrGI digested 5987-nt pACD-ΔORF+ORF2EBS1+2/OS vector DNA at 16° C. for overnight. The ligation products were then phenol-CIA extracted and ethanol precipitated in the presence of 10 μg of carrier *E. coli* tRNA (sigma, St Louis, Mo.). The pellet was washed with 70% ethanol and air dried before resuspended in 150 ml 0.5×TE (5 mM Tris-HCl (pH 7.5), 0.5 mM EDTA).

To amplify the library, ligation products were transformed into *E. coli* DH10B cells. Each time 1 μl of the ligation products and 40 μl *E. coli* DH10B cells were mixed, electroporated in a 0.1 cm electroporation cuvette with voltage setting at 2.0 kilovolts using Bio-Rad *E. coli* pulser (Bio-Rad Laboratories, Hercules, Calif.) and 30 independent transformations were carried out. The electroporated cells were immediately inoculated into appropriate SOC bacterial growth media without any antibiotics for 1 hour for rescue and small aliquots of cells were plated on LB plates containing 25 μg/ml chloramphenicol and grow at 37° C. overnight to estimate the total number of independent transformants. The remaining transformed cells were inoculated into liquid LB medium containing 25 μg/ml chloramphenicol and grown overnight at 37° C. to amplify the library. Assuming that most or all of the independent transformants would be different from each other, the diversity of the library was estimated to be the number of total independent transformants. But in this case, the diversity would be twice the amount of the total independent transformants because the IBS, EBS1 and S region were randomized and unpaired in most of the fragment cloned in the pACD-ΔORF+ORF2EBS1+2/OS due to randomization of IBS, EBS1 and S region in the oligonucleotides LIBSN12 and LEBS1N9 used in the final PCR. Therefore, each plasmid transformed would make two different plasmids after replication. The diversity of the library was made to be $2.2 \times 10^8$.

Oligos used in library construction are:

LIBSN12:

5'-AAA AAA GCT TCG TCG ATC GTG AAN NNN NNN NNN NNG TGC GCC CAG ATA GGG TG-3' (SEQ ID NO: 7)

LtrBAsEBS2:

5'-AAC CGA AAT TAG AAA CTT GCG TTC AG-3' (SEQ ID NO: 8)

LEBS1N9:

5'-CAG ATT GTA CAA ATG TGG TGA TAA CAG ATA AGT CNN NNN NNN NAA CTT ACC TTT CTT TGT-3' (SEQ ID NO: 9)

LEBS2N9:

5'-CGC AAG TTT CTA ATT TCG GTT NNN NNT CGA TAG AGG AAA GTG TCT-3' (SEQ ID NO: 10).

The "N" in each oligo indicates each randomized position.

Example 5

Iterative Selection for Most Efficient introns from a Combinatorial Donor Plasmid Library Example 3 describes a method of identifying specific group II introns, from a library of donor plasmids containing different modified group II introns, that integrate into a specific DNA target site. The goal of such a scheme is to isolate the specific group II introns that efficiently integrate into the chosen target recognition site. This example describes an iterative, enrichment step that can be added to the steps described in Example 3 that facilitates identification and isolation of introns that most efficiently integrate into a target recognition site of choice.

Figure 6:
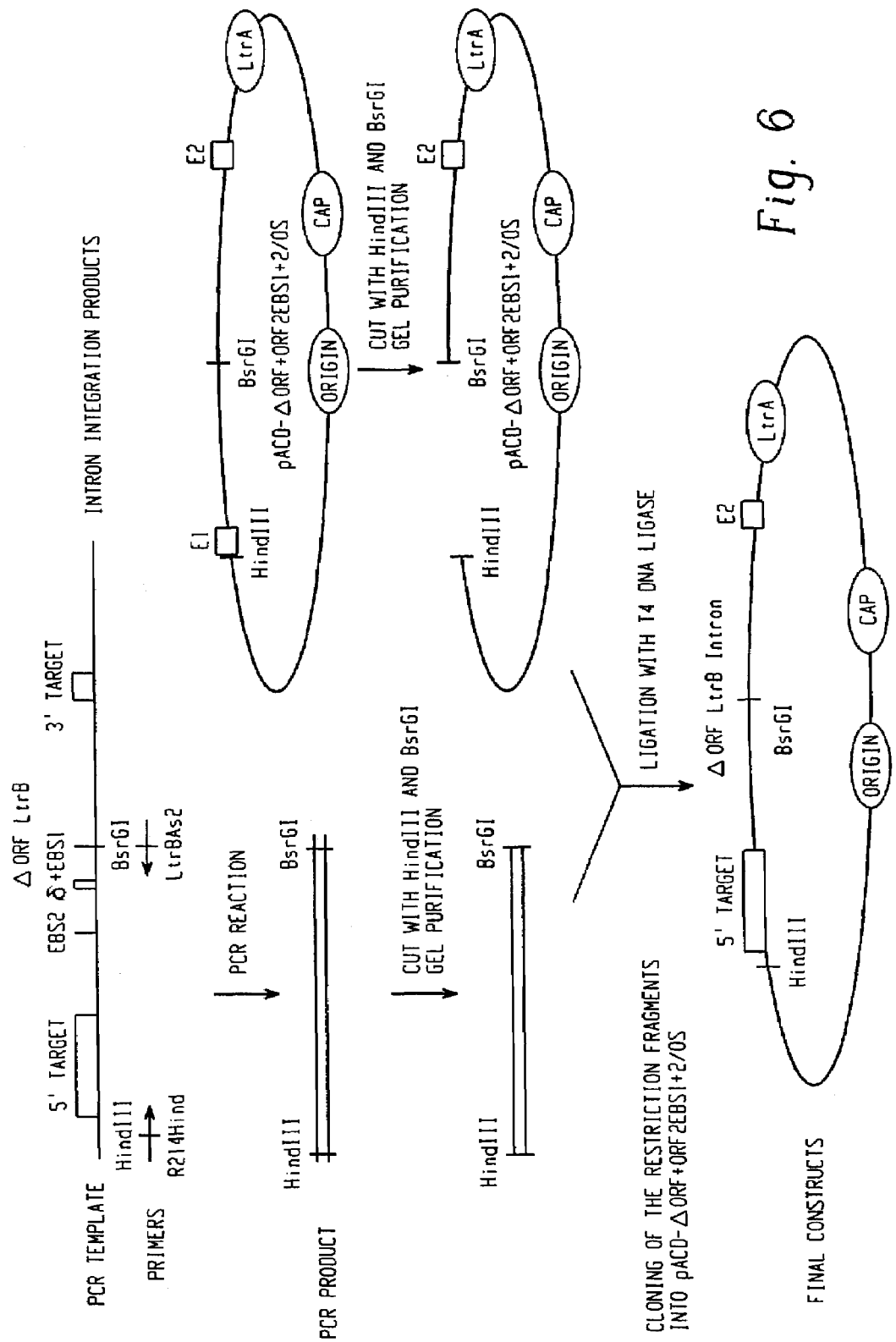
FIG. 6. Schematic representation of donor plasmid library regeneration for second round selection.

The procedure of enriching for introns that efficiently integrate into a chosen target site is shown in FIG. 6. In this procedure, the genetic assay (FIG. 1) is performed as described in Example 3, with the following modifications. Plasmid DNA of the $Tet^R$ transformants from the initial selection are isolated. The target site fragments, containing the inserted introns, are then amplified by PCR and inserted into a new donor plasmid for a second round of selection. Because the introns select sites that have complementary IBS and δ' sequences, they have no problem splicing out of these sites for the second round of selection. Additional selection rounds are performed to isolate introns that insert most efficiently.

```

What is claimed is:

1. A method of increasing insertion of modified group II introns into a DNA target site in a host cell in vitro, comprising:
   a) introducing a nucleic acid construct into the host cell, said construct comprising:
      i.) a modified group II intron sequence encoding a modified group II intron RNA, said modified group II intron RNA comprising an EBS1 sequence, an EBS2 sequence, a delta sequence, and a deletion of subdomains IVB1, IVB2, IVB3, wherein one or more of said EBS1, EBS2 or delta sequences is modified to provide a modified EBS1, EBS2, and delta sequence that base pairs with an IBS1, IBS2, and delta prime sequence, respectively, in the DNA target site;
      ii) a promoter for regulating transcription of said modified group II intron sequence, said promoter being operably linked to the modified group II intron sequence;
      iii) a first flanking sequence upstream of the modified group II intron sequence, said flanking sequence encoding a first hybridizing sequence which is complementary to the EBS1 or the modified EBS1 sequence contained in said modified group II intron RNA, and a second flanking sequence downstream of the modified group II intron sequence encoding a second hybridizing sequence which is complementary to the EBS2 or the modified EBS2 sequence contained in said modified group II intron RNA; and
      iv) an open reading frame sequence encoding a wild-type or modified group II intron encoded protein, wherein said open reading frame sequence is located upstream, or downstream of the modified group II intron sequence, and wherein expression of said group II intron encoded protein is regulated by the promoter which is operably linked to the modified group II intron sequence or by a second promoter which is operably linked to the open reading frame sequence; and
   b) maintaining the cell under in vitro conditions which allow for expression of the modified group II intron sequence and the open reading frame sequence, formation of RNP particles comprising a modified excised group II intron RNA which is encoded by the modified group II intron sequence and a group II intron encoded protein which is encoded by the open reading frame sequence, and insertion of the modified group II intron into the DNA target site;
   wherein the method results in increased insertion of said modified group II introns into the DNA target site in the host cell in vitro as compared to a method where the group II intron RNA lacks deletion of subdomains IVB1, IVB2, and IVB3.

2. A method of increasing insertion of modified group II introns into a DNA target site in a host cell in vitro, said method comprising:
   a) introducing a nucleic acid construct into the host cell, said construct comprising
      i.) a modified L1.LtrB intron sequence encoding a modified group II intron RNA, said modified group II intron RNA comprising an EBS1 sequence, an EBS2 sequence, a delta sequence, and a deletion of subdomains IVB1, IVB2, IVB3, wherein one or more of said EBS1, EBS2 or delta sequences is modified to provide a modified EBS1, EBS2, and delta sequence that base pairs with an IBS1, IBS2, and delta prime sequence, respectively, in the DNA target site;
      ii) a promoter for regulating transcription of said modified group II intron sequence, said promoter being operably linked to the modified L1.LtrB intron sequence;
      iii) a first flanking sequence upstream of the modified L1.LtrB intron sequence, said flanking sequence encoding a first hybridizing sequence which is complementary to the EBS1 or the modified EBS1 sequence contained in the modified group II intron RNA and a second flanking sequence downstream of the modified L1.LtrB sequence encoding a second hybridizing sequence which is complementary to the EBS2 or the modified EBS2 sequence contained in the modified group II intron RNA; and
      iv) an open reading frame sequence encoding a modified or wild-type LtrA protein,
         wherein said open reading frame sequence is located upstream, or downstream of the modified L1.LtrB intron sequence, and
         wherein expression of said LtrA protein is regulated by the promoter which is operably linked to the modified L1.LtrB intron sequence or by a second promoter which is operably linked to the open reading frame sequence; and
   b) maintaining the cell under in vitro conditions which allow for expression of the modified L1.LtrB intron sequence and the open reading frame sequence, formation of modified group II RNP particles and the modified or wild-type LtrA protein, and insertion of the modified group II intron into the DNA target site;
      wherein the method results in increased insertion of said modified group II introns into the DNA target site in the host cell in vitro as compared to a method where the group II intron RNA lacks deletion of subdomains IVB1, IVB2, and IVB3.

3. The method of claim 1 wherein the nucleic acid construct is introduced into the host cell via a viral vector.

4. The method of claim 1 wherein the nucleic acid construct is introduced into the host cell in association with a liposome.

5. The method of claim 1 wherein the nucleic acid construct is introduced into the host cell via a plasmid.

6. The method of claim 1 wherein the host cell is an archaebacterial or eubacterial cell.

7. The method of claim 1 wherein the host cell is a fungal cell, a plant cell or algae cell.

8. The method of claim 1 wherein the host cell is an animal cell.

9. The method of claim 1 wherein the group II intron encoded protein is modified at the N-terminus, the C-terminus, or internally and wherein the open reading frame encodes a fusion protein comprising a group II intron encoded protein linked to a purification tag, a detection tag or an intracellular localization signal.

10. A method of increasing insertion of modified group II introns into a DNA target site in a host cell in vitro, comprising:
   a) introducing a nucleic acid construct into the host cell, said construct comprising
      i.) a modified group II intron sequence encoding a modified group II intron RNA, said modified group II intron RNA comprising an EBS1 sequence, an EBS2 sequence, a delta sequence, and a deletion of subdomains IVB1, IVB2, IVB3, wherein one or more of said EBS1, EBS2 or delta sequences is modified to provide a modified EBS1, EBS2, and delta sequence that base pairs with an IBS1, IBS2, and delta prime sequence, respectively, in the DNA target site;
      ii) a promoter for regulating transcription of said modified group II intron sequence, said promoter being operably linked to the modified group II intron sequence;
      iii) a first flanking sequence upstream of the group II intron sequence, said flanking sequence encoding a first hybridizing sequence which is complementary to the EBS1 or the modified EBS1 sequence contained in said modified group II intron RNA and a second flanking sequence downstream of the modified group II intron sequence encoding a second hybridizing sequence which is complementary to the EBS2 or the modified EBS2 sequence contained in said modified group II intron RNA; and
   b) introducing a second nucleic acid construct into the cell, said second construct comprising an open reading frame sequence encoding a wild-type or modified group II intron encoded protein and a promoter which is operably linked to the open reading frame sequence; and
   c) maintaining the cell under in vitro conditions which allow for expression of the modified group II intron sequence and the open reading frame sequence, formation of RNP particles comprising a modified excised group II intron RNA which is encoded by the modified group II intron sequence and a group II intron encoded protein which is encoded by the open reading frame sequence, and insertion of the modified group II intron into the DNA target site;
   wherein the method results in increased insertion of said modified group II introns into a DNA target site in the host cell in vitro as compared to a method where the group II intron RNA lacks deletion of subdomains IVB1, IVB2, and IVB3.

11. The method of claim 10 wherein the group II intron encoded protein is modified at the N-terminus, the C-terminus, or internally and wherein the open reading frame encodes a fusion protein comprising a group II intron encoded protein linked to a purification tag, a detection tag, or an intracellular localization signal.

12. The method of claim 1, wherein the modified group II intron RNA comprises a modified EBS1 sequence.

13. The method of claim 1, wherein the modified group II intron RNA comprises a modified EBS2 sequence.

14. The method of claim 1, wherein the modified group II intron RNA comprises a modified delta sequence.

15. The method of claim 10 wherein the modified group II intron is a modified L1.LtrB intron, and wherein the open reading frame sequence encodes a wild-type or modified LtrA protein.

16. The method of claim 1, wherein the RNP particles prepared by said method have greater resistance to nucleolytic activity in the host cell than RNP particles comprising a group II intron RNA lacking deletion of subdomains IVB1, IVB2, and IVB3.

17. The method of claim 2, wherein the RNP particles prepared by said method have greater resistance to nucleolytic activity in the host cell than RNP particles comprising a group II intron RNA lacking deletion of subdomains IVB1, IVB2, and IVB3.

18. The method of claim 10, wherein the RNP particles prepared by said method have greater resistance to nucleolytic activity in the host cell than RNP particles comprising a group II intron RNA lacking deletion of subdomains IVB1, IVB2, and IVB3.

* * * * *

UNITED STATES PATENT AND TRADEMARK OFFICE
CERTIFICATE OF CORRECTION

PATENT NO. : 7,592,161 B2  Page 1 of 1
APPLICATION NO. : 10/277643
DATED : September 22, 2009
INVENTOR(S) : Lambowitz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 926 days.

Signed and Sealed this

Fourteenth Day of December, 2010

David J. Kappos
*Director of the United States Patent and Trademark Office*

                        SEQUENCE LISTING

<160> NUMBER OF SEQ ID NOS: 11

<210> SEQ ID NO 1
<211> LENGTH: 79
<212> TYPE: DNA
<213> ORGANISM: Lactococcus lactis

<400> SEQUENCE: 1
gcggcgacgt cacccacgtc gatcgtgaac acatccataa ccatatcatt tttaatgaat      60
tcgataccgt cgacctcga                                                  79

<210> SEQ ID NO 2
<211> LENGTH: 17
<212> TYPE: DNA
<213> ORGANISM: Lactococcus lactis

<400> SEQUENCE: 2
tcgaggtcga cggtatc                                                    17

<210> SEQ ID NO 3
<211> LENGTH: 53
<212> TYPE: DNA
<213> ORGANISM: Artificial
<220> FEATURE:
<223> OTHER INFORMATION: Primer for PCR amplification.
<220> FEATURE:
<221> NAME/KEY: misc_feature
<222> LOCATION: (23)..(23)
<223> OTHER INFORMATION: n = a or t or g or c
<220> FEATURE:
<221> NAME/KEY: misc_feature
```

```
<222> LOCATION: (24)..(24)
<223> OTHER INFORMATION: n = a or t or g or c
<220> FEATURE:
<221> NAME/KEY: misc_feature
<222> LOCATION: (25)..(25)
<223> OTHER INFORMATION: n = a or t or g or c
<220> FEATURE:
<221> NAME/KEY: misc_feature
<222> LOCATION: (26)..(26)
<223> OTHER INFORMATION: n = a or t or g or c
<220> FEATURE:
<221> NAME/KEY: misc_feature
<222> LOCATION: (27)..(27)
<223> OTHER INFORMATION: n = a or t or g or c
<220> FEATURE:
<221> NAME/KEY: misc_feature
<222> LOCATION: (28)..(28)
<223> OTHER INFORMATION: n = a or t or g or c
<220> FEATURE:
<221> NAME/KEY: misc_feature
<222> LOCATION: (29)..(29)
<223> OTHER INFORMATION: n = a or t or g or c
<220> FEATURE:
<221> NAME/KEY: misc_feature
<222> LOCATION: (30)..(30)
<223> OTHER INFORMATION: n = a or t or g or c
<220> FEATURE:
<221> NAME/KEY: misc_feature
<222> LOCATION: (31)..(31)
<223> OTHER INFORMATION: n = a or t or g or c
<220> FEATURE:
<221> NAME/KEY: misc_feature
<222> LOCATION: (32)..(32)
<223> OTHER INFORMATION: n = a or t or g or c
<220> FEATURE:
<221> NAME/KEY: misc_feature
<222> LOCATION: (33)..(33)
<223> OTHER INFORMATION: n = a or t or g or c
<220> FEATURE:
<221> NAME/KEY: misc_feature
<222> LOCATION: (34)..(34)
<223> OTHER INFORMATION: n = a or t or g or c
<220> FEATURE:
<221> NAME/KEY: misc_feature
<222> LOCATION: (35)..(35)
<223> OTHER INFORMATION: n = a or t or g or c

<400> SEQUENCE: 3
aaaaaagctt cgtcgatcgt gannnnnnnn nnnnngtgcg cccagatagg gtg         53

<210> SEQ ID NO 4
<211> LENGTH: 26
<212> TYPE: DNA
<213> ORGANISM: Lactococcus lactis

<400> SEQUENCE: 4
aaccgaaatt agaaacttgc gttcag                                       26

<210> SEQ ID NO 5
<211> LENGTH: 60
<212> TYPE: DNA
<213> ORGANISM: Artificial
<220> FEATURE:
<223> OTHER INFORMATION: Primer for PCR amplification.
<220> FEATURE:
<221> NAME/KEY: misc_feature
<222> LOCATION: (35)..(35)
<223> OTHER INFORMATION: n = a or t or g or c
<220> FEATURE:
<221> NAME/KEY: misc_feature
<222> LOCATION: (36)..(36)
<223> OTHER INFORMATION: n = a or t or g or c
<220> FEATURE:
<221> NAME/KEY: misc_feature
<222> LOCATION: (37)..(37)
```

```
<223> OTHER INFORMATION: n = a or t or g or c
<220> FEATURE:
<221> NAME/KEY: misc_feature
<222> LOCATION: (38)..(38)
<223> OTHER INFORMATION: n = a or t or g or c
<220> FEATURE:
<221> NAME/KEY: misc_feature
<222> LOCATION: (39)..(39)
<223> OTHER INFORMATION: n = a or t or g or c
<220> FEATURE:
<221> NAME/KEY: misc_feature
<222> LOCATION: (40)..(40)
<223> OTHER INFORMATION: n = a or t or g or c
<220> FEATURE:
<221> NAME/KEY: misc_feature
<222> LOCATION: (41)..(41)
<223> OTHER INFORMATION: n = a or t or g or c
<220> FEATURE:
<221> NAME/KEY: misc_feature
<222> LOCATION: (42)..(42)
<223> OTHER INFORMATION: n = a or t or g or c
<220> FEATURE:
<221> NAME/KEY: misc_feature
<222> LOCATION: (43)..(43)
<223> OTHER INFORMATION: n = a or t or g or c
<220> FEATURE:
<221> NAME/KEY: misc_feature
<222> LOCATION: (44)..(44)
<223> OTHER INFORMATION: n = a or t or g or c

<400> SEQUENCE: 5
cagattgtac aaatgtggtg ataacagata agtcnnnnnn nnnnacttac ctttctttgt      60

<210> SEQ ID NO 6
<211> LENGTH: 45
<212> TYPE: DNA
<213> ORGANISM: Artificial
<220> FEATURE:
<223> OTHER INFORMATION: Primer for PCR amplification.
<220> FEATURE:
<221> NAME/KEY: misc_feature
<222> LOCATION: (22)..(22)
<223> OTHER INFORMATION: n = a or t or g or c
<220> FEATURE:
<221> NAME/KEY: misc_feature
<222> LOCATION: (23)..(23)
<223> OTHER INFORMATION: n = a or t or g or c
<220> FEATURE:
<221> NAME/KEY: misc_feature
<222> LOCATION: (24)..(24)
<223> OTHER INFORMATION: n = a or t or g or c
<220> FEATURE:
<221> NAME/KEY: misc_feature
<222> LOCATION: (25)..(25)
<223> OTHER INFORMATION: n = a or t or g or c
<220> FEATURE:
<221> NAME/KEY: misc_feature
<222> LOCATION: (26)..(26)
<223> OTHER INFORMATION: n = a or t or g or c
<220> FEATURE:
<221> NAME/KEY: misc_feature
<222> LOCATION: (27)..(27)
<223> OTHER INFORMATION: n = a or t or g or c

<400> SEQUENCE: 6
cgcaagtttc taatttcggt tnnnnnncga tagaggaaag tgtct                      45

<210> SEQ ID NO 7
<211> LENGTH: 53
<212> TYPE: DNA
<213> ORGANISM: Artificial
<220> FEATURE:
<223> OTHER INFORMATION: Primer for PCR amplification.
<220> FEATURE:
<221> NAME/KEY: misc_feature
```

```
<222> LOCATION: (24)..(24)
<223> OTHER INFORMATION: n = a or t or g or c
<220> FEATURE:
<221> NAME/KEY: misc_feature
<222> LOCATION: (25)..(25)
<223> OTHER INFORMATION: n = a or t or g or c
<220> FEATURE:
<221> NAME/KEY: misc_feature
<222> LOCATION: (26)..(26)
<223> OTHER INFORMATION: n = a or t or g or c
<220> FEATURE:
<221> NAME/KEY: misc_feature
<222> LOCATION: (27)..(27)
<223> OTHER INFORMATION: n = a or t or g or c
<220> FEATURE:
<221> NAME/KEY: misc_feature
<222> LOCATION: (28)..(28)
<223> OTHER INFORMATION: n = a or t or g or c
<220> FEATURE:
<221> NAME/KEY: misc_feature
<222> LOCATION: (29)..(29)
<223> OTHER INFORMATION: n = a or t or g or c
<220> FEATURE:
<221> NAME/KEY: misc_feature
<222> LOCATION: (30)..(30)
<223> OTHER INFORMATION: n = a or t or g or c
<220> FEATURE:
<221> NAME/KEY: misc_feature
<222> LOCATION: (31)..(31)
<223> OTHER INFORMATION: n = a or t or g or c
<220> FEATURE:
<221> NAME/KEY: misc_feature
<222> LOCATION: (32)..(32)
<223> OTHER INFORMATION: n = a or t or g or c
<220> FEATURE:
<221> NAME/KEY: misc_feature
<222> LOCATION: (33)..(33)
<223> OTHER INFORMATION: n = a or t or g or c
<220> FEATURE:
<221> NAME/KEY: misc_feature
<222> LOCATION: (34)..(34)
<223> OTHER INFORMATION: n = a or t or g or c
<220> FEATURE:
<221> NAME/KEY: misc_feature
<222> LOCATION: (35)..(35)
<223> OTHER INFORMATION: n = a or t or g or c

<400> SEQUENCE: 7
aaaaaagctt cgtcgatcgt gaannnnnnn nnnnngtgcg cccagatagg gtg          53

<210> SEQ ID NO 8
<211> LENGTH: 26
<212> TYPE: DNA
<213> ORGANISM: Lactococcus lactis

<400> SEQUENCE: 8
aaccgaaatt agaaacttgc gttcag                                        26

<210> SEQ ID NO 9
<211> LENGTH: 60
<212> TYPE: DNA
<213> ORGANISM: Artificial
<220> FEATURE:
<223> OTHER INFORMATION: Primer for PCR amplification.
<220> FEATURE:
<221> NAME/KEY: misc_feature
<222> LOCATION: (35)..(35)
<223> OTHER INFORMATION: n = a or t or g or c
<220> FEATURE:
<221> NAME/KEY: misc_feature
<222> LOCATION: (36)..(36)
<223> OTHER INFORMATION: n = a or t or g or c
<220> FEATURE:
<221> NAME/KEY: misc_feature
<222> LOCATION: (37)..(37)
```

```
<223> OTHER INFORMATION: n = a or t or g or c
<220> FEATURE:
<221> NAME/KEY: misc_feature
<222> LOCATION: (38)..(38)
<223> OTHER INFORMATION: n = a or t or g or c
<220> FEATURE:
<221> NAME/KEY: misc_feature
<222> LOCATION: (39)..(39)
<223> OTHER INFORMATION: n = a or t or g or c
<220> FEATURE:
<221> NAME/KEY: misc_feature
<222> LOCATION: (40)..(40)
<223> OTHER INFORMATION: n = a or t or g or c
<220> FEATURE:
<221> NAME/KEY: misc_feature
<222> LOCATION: (41)..(41)
<223> OTHER INFORMATION: n = a or t or g or c
<220> FEATURE:
<221> NAME/KEY: misc_feature
<222> LOCATION: (42)..(42)
<223> OTHER INFORMATION: n = a or t or g or c
<220> FEATURE:
<221> NAME/KEY: misc_feature
<222> LOCATION: (43)..(43)
<223> OTHER INFORMATION: n = a or t or g or c

<400> SEQUENCE: 9
cagattgtac aaatgtggtg ataacagata agtcnnnnnn nnnaacttac ctttctttgt      60

<210> SEQ ID NO 10
<211> LENGTH: 45
<212> TYPE: DNA
<213> ORGANISM: Artificial
<220> FEATURE:
<223> OTHER INFORMATION: Primer for PCR amplification.
<220> FEATURE:
<221> NAME/KEY: misc_feature
<222> LOCATION: (22)..(22)
<223> OTHER INFORMATION: n = a or t or g or c
<220> FEATURE:
<221> NAME/KEY: misc_feature
<222> LOCATION: (23)..(23)
<223> OTHER INFORMATION: n = a or t or g or c
<220> FEATURE:
<221> NAME/KEY: misc_feature
<222> LOCATION: (24)..(24)
<223> OTHER INFORMATION: n = a or t or g or c
<220> FEATURE:
<221> NAME/KEY: misc_feature
<222> LOCATION: (25)..(25)
<223> OTHER INFORMATION: n = a or t or g or c
<220> FEATURE:
<221> NAME/KEY: misc_feature
<222> LOCATION: (26)..(26)
<223> OTHER INFORMATION: n = a or t or g or c

<400> SEQUENCE: 10
cgcaagtttc taatttcggt tnnnnntcga tagaggaaag tgtct                      45

<210> SEQ ID NO 11
<211> LENGTH: 2761
<212> TYPE: DNA
<213> ORGANISM: Lactococcus lactis

<400> SEQUENCE: 11
aagcttagag aaaaataatg cggtgcttgg tcatcacctc atccaatcat tttctcctga      60
tgacaatcta actcctgaac aaattcatga ataggtcgt caaaccatat tagaatttac     120
aggtggcgaa tatgaatttg tgattgcaac ccacgtcgat cgtgaacaca tccataacgt     180
gcgcccagat agggtgttaa gtcaagtagt ttaaggtact actctgtaag ataacacaga     240
aaacagccaa cctaaccgaa aagcgaaagc tgatacggga acagagcacg gttggaaagc     300
```

```
gatgagttac ctaaagacaa tcgggtacga ctgagtcgca atgttaatca gatataaggt    360
ataagttgtg tttactgaac gcaagtttct aatttcggtt atgtgtcgat agaggaaagt    420
gtctgaaacc tctagtacaa agaaaggtaa gttatggttg tggacttatc tgttatcacc    480
acatttgtac aatctgtagg agaacctatg ggaacgaaac gaaagcgatg ccgagaatct    540
gaatttacca agacttaaca ctaactgggg atacccctaaa caagaatgcc taatagaaag    600
gaggaaaaag gctatagcac tagagcttga aaatcttgca agggtacgga gtactcgtag    660
tattctgaga agggtaacgc cctttacatg gcaaaggggt acagttattg tgtactaaaa    720
ttaaaaattg attagggagg aaaacctcaa aatgaaacca acaatggcaa ttttagaaag    780
aatcagtaaa aattcacaag aaaatataga cgaagttttt acaagacttt atcgttatct    840
tttacgtcca gatatttatt acgtggcgta tcaaaattta tattccaata aaggagcttc    900
cacaaaagga atattagatg atacagcgga tggctttagt gaagaaaaaa taaaaaagat    960
tattcaatct ttaaaagacg gaacttacta tcctcaacct gtacgaagaa tgtatattgc   1020
aaaaaagaat tctaaaaaga tgagacccttt aggaattcca actttcacag ataaattgat   1080
ccaagaagct gtgagaataa ttcttgaatc tatctatgaa ccggtattcg aagatgtgtc   1140
tcacggtttt agacctcaac gaagctgtca cacagctttg aaaacaatca aaagagagtt   1200
tggcggcgca agatggtttg tggagggaga tataaaaggc tgcttcgata atatagacca   1260
cgttacactc attggactca tcaatcttaa aatcaaagat atgaaaatga gccaattgat   1320
ttataaattt ctaaaagcag gttatctgga aaactggcag tatcacaaaa cttacagcgg   1380
aacacctcaa ggtggaattc tatctcctct tttggccaac atctatcttc atgaattgga   1440
taagtttgtt ttacaactca aaatgaagtt tgaccgagaa agtccagaaa gaataacacc   1500
tgaatatcgg gaacttcaca atgagataaa aagaatttct caccgtctca agaagttgga   1560
gggtgaagaa aaagctaaag ttcttttaga atatcaagaa aaacgtaaaa gattacccac   1620
actcccctgt acctcacaga caaataaagt attgaaatac gtccggtatg cggacgactt   1680
cattatctct gttaaaggaa gcaaagagga ctgtcaatgg ataaaagaac aattaaaact   1740
ttttattcat aacaagctaa aaatggaatt gagtgaagaa aaaacactca tcacacatag   1800
cagtcaaccc gctcgttttc tgggatatga tatacgagta aggagaagtg gaacgataaa   1860
acgatctggt aaagtcaaaa agagaacact caatgggagt gtagaactcc ttattcctct   1920
tcaagacaaa attcgtcaat ttattttga caagaaaata gctatccaaa agaaagatag   1980
ctcatggttt ccagttcaca ggaaatatct tattcgttca acagacttag aaatcatcac   2040
aatttataat tctgaattaa gagggatttg taattactac ggtctagcaa gtaattttaa   2100
ccagctcaat tattttgctt atcttatgga atacagctgt ctaaaaacga tagcctccaa   2160
acataaggga acactttcaa aaaccatttc catgttttaaa gatggaagtg gttcgtgggg   2220
catcccgtat gagataaagc aaggtaagca gcgccgttat tttgcaaatt ttagtgaatg   2280
taaatcccct tatcaatttta cggatgagat aagtcaagct cctgtattgt atggctatgc   2340
ccggaatact cttgaaaaca ggttaaaagc taaatgttgt gaattatgtg aacatctga    2400 tgaaaatact tcctatgaaa ttcaccatgt caataaggtc aaaaatctta aaggcaaaga   2460
aaaatgggaa atggcaatga tagcgaaaca acgtaaaaact cttgttgtat gctttcattg   2520
tcatcgtcac gtgattcata acacaagtga aattttttacg aacgaacaat aacagagccg   2580
tatactccga gaggggtacg tacggttccc gaagagggtg gtgcaaacca gtcacagtaa   2640
```

```
                                                        -continued tgtgaacaag gcggtacctc cctacttcac catatcattt ttaattctac gaatctttat    2700
actggcaaac aatttgactg gaaagtcatt cctaaagaga aaacaaaaag cggcaaagct    2760
t                                                                    2761
```